United States Patent [19]

Côté et al.

[11] Patent Number: 5,510,248
[45] Date of Patent: Apr. 23, 1996

[54] STABLE RECOMBINANT MEIZOTHROMBIN-LIKE POLYPEPTIDES

[75] Inventors: Hélène C. F. Côté, Vancouver; Willem K. Stevens; Michael E. Nesheim, both of Kingston; Ross T. A. MacGillivray, Vancouver, all of Canada

[73] Assignee: The University of British Columbia, Canada

[21] Appl. No.: 82,843

[22] Filed: Jun. 22, 1993

[51] Int. Cl.$^6$ .............................. C12P 21/02; C12N 5/10; C12N 15/11; C07H 21/04

[52] U.S. Cl. .................. 435/69.6; 435/240.2; 435/320.1; 536/23.2; 536/23.5

[58] Field of Search ................................ 435/69.6, 172.3, 435/240.2, 252.3, 255, 320.1; 536/23.2, 23.5

[56] References Cited

U.S. PATENT DOCUMENTS 5,288,629  2/1994  Berkner ................................ 435/240.2

OTHER PUBLICATIONS

Pei et al (1991) J. Biol Chem 266, 9598–9604.
Coté et al., The Journal of Biological Chemistry, vol. 269, No. 15; pp. 11374–11380; Apr. 15, 1994.
Sandra J. Friezner Degen, et al., Characterization of the Complementary . . . Biochemistry, vol. 22, No. 9, pp. 2087–2097, 1983.
Sandra J. Friezner Degen, et al., Nucleotide Sequence of the Gene for Human . . . Biochemistry, vol. 26, No. 19, pp. 6166–6177, 1987.
Ross T. A. MacGillivray, et al., Recombinant Genetic Approaches to Functional . . . Annals of the New York Academy of Sciences, vol. 485, pp. 73–79.
Maria T. Jorgensen, et al., Expression of Completely y-Carboxylated . . . The Journal of Biological Chemistry, vol. 202, pp. 6729–6734, May 1987.
Bernard F. Le Bonniec, et al., Thrombin Glu–39 Restricts the P'3 . . . The Journal of Biological Chemistry, vol. 266, No. 21, pp. 13796–13803, Jul. 1991.
F. G. Falkner, et al., High Level Expression of Active Human Prothrombin . . . Thrombosis and Haemostasis, vol. 68, No. 2, pp. 119–124, 1992.
John P. Sheehan, et al., Mutagenesis of Thrombin Selectively Modulates . . . The Journal of Biological Chemistry, vol. 268, No. 5, pp. 3639–3645, Feb. 15, 1993.
Qingyu Wu, et al., Single amino acid substitutions dissociate fibrinogen . . . Proc Nat'l Acad. Sci, USA, vol. 88, pp. 6775–6779, Aug. 1991.
Qingyu Wu, et al., Ligand Specificity of Human Thrombomodulin The Journal of Biologcial Chemistry, vol. 267, No. 10, pp. 7083–7088, Apr. 5, 1992.
Bernard F. Le Bonniec, et al., Interaction of Thrombin des–ETW with . . . The Journal of Biological Chemistry, vol. 267, No. 27, pp. 19341–19346, Sep. 25, 1992.
Bernard F. Le Bonniec, et al., The Role of Calcium Ions in Factor X Activation . . . The Journal of Biological Chemistry, vol. 267, No. 10, pp. 6970–6976, Apr. 5, 1992.
Bernard F. Le Bonniec, et al., Glu–192–Gln substitution in thrombin mimics . . . Proc. Nat'l Acad. Sci, USA, vol. 88, pp. 7371–7375, Aug. 1991.
Margaret F. Doyle, et al., Multiple Active Forms of Thrombin The Journal of Biological Chemistry, vol. 265, No. 18, pp. 10693–10701, Jun. 25, 1990.
Jan Rosing, et al., Formation of Meizothrombin as Intermediate in Factor . . . The Journal of Biological Chemistry, vol. 261, No. 9, pp. 4224–4228, Mar. 25, 1986.
Guido Tans, et al., Meizothrombin Formation during Factor Xa–catalyzed . . . The Journal of Biological Chemistry, vol. 266, No. 32, pp. 21864–21873, Nov. 15, 1991.
Jan Rosing, et al., Meizothrombin, a Major Product of Factor $X_a$–Catalyzed . . . Thrombosis and Haemostasis, vol. 60, No. 3, pp. 355–360, 1988.
Guido Tans, et al., Amidolytic Detection of Prothrombin Activation Products . . . Thrombosis and Haemostasis, vol. 61, No. 3, 386–391, 1989.
Sriram Krishnaswamy, et al., The Prothrombinase–catalyzed Activation of . . . The Journal of Biological Chemistry, vol. 261, No. 19, pp. 8977–8984, Jul. 5, 1986.
Danilo S. Boskovic, et al., Studies of the Role of Factor Va in the Factor . . . The Journal of Biological Chemistry, vol. 265, No. 18, pp. 10497–10505, Jun. 25, 1990.
Pim N. M. Tijburg, et al., Formation of Meizothrombin as Intermediate in Factor . . . The Journal of Biological Chemistry, vol. 266, No. 6, pp. 4017–4022, Feb. 25, 1991.
Scott A. Armstrong, et al., The Active Site of Membrane–bound Meizothrombin The Journal of Biological Chemistry, vol. 265, No. 11, pp. 6210–6218, Apr. 15, 1990.
Charles T. Esmon, et al., The Conversion of Prothrombin to Thrombin The Journal of Biological Chemistry, vol. 249, No. 2, pp. 607–611, Jan. 25, 1974.
Whyte G. Owen, et al., The Conversion of Prothrombin to Thrombin The Journal of Biological Chemistry, vol. 249, No. 2, pp. 594–605, Jan. 25, 1974.
Jan Rosing, et al., The Role of Phospholipids and Factor $V_a$ in the Prothrombinase The Journal of Biological Chemistry, vol. 255, No. 1, pp. 274–283, Jan. 10, 1980.

Primary Examiner—George C. Elliott
Attorney, Agent, or Firm—Fish & Richardson

[57] ABSTRACT

An isolated polynucleotide which encodes human prothrombin is modified to encode amino acid substitutions at positions 155, 271 and 284 of the prothrombin polypeptide. A second polynucleotide is further modified to encode an additional amino acid substitution at residue 320.

The polypeptide encoded by the first polynucleotide is resistant to cleavage by thrombin and factor Xa, exhibits greatly reduced procoagulant activity towards fibrinogen and unchanged anticoagulant activity towards protein C. The polypeptide can be cleaved between amino acid positions 320 and 321 to produce an active serine protease which can activate protein C, thereby inhibiting coagulation and stimulating activated protein C fibrinolytic activity.

The polypeptide encoded by the second polynucleotide cannot be cleaved, mimics inactive prothrombin and thereby acts as a reversible inhibitor of coagulation by competing with Factor Xa and Factor Va for interaction at the phospholipid surface.

Methods of producing recombinant polypeptides using the two isolated, modified polynucleotides are described.

20 Claims, 10 Drawing Sheets

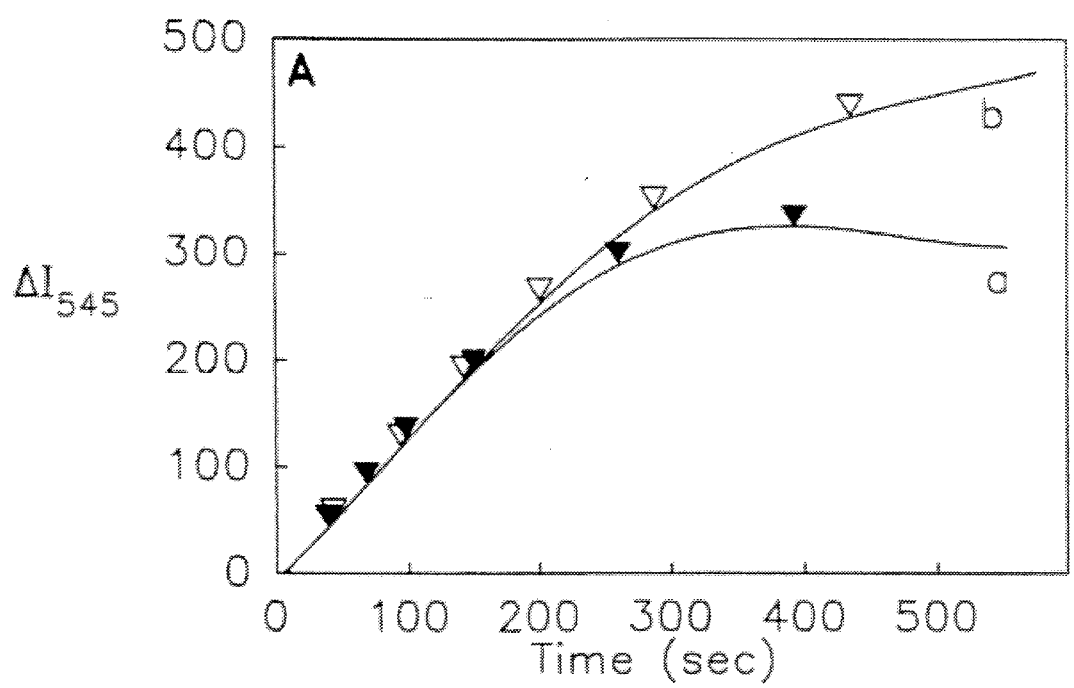
FIG. 6A
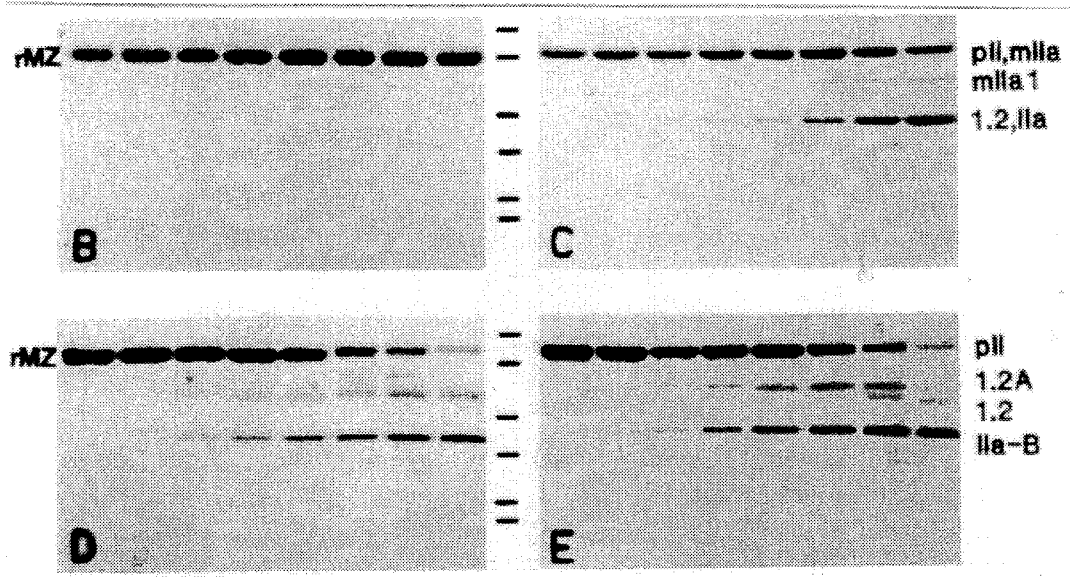
FIG. 6B    FIG. 6C
FIG. 6D    FIG. 6E

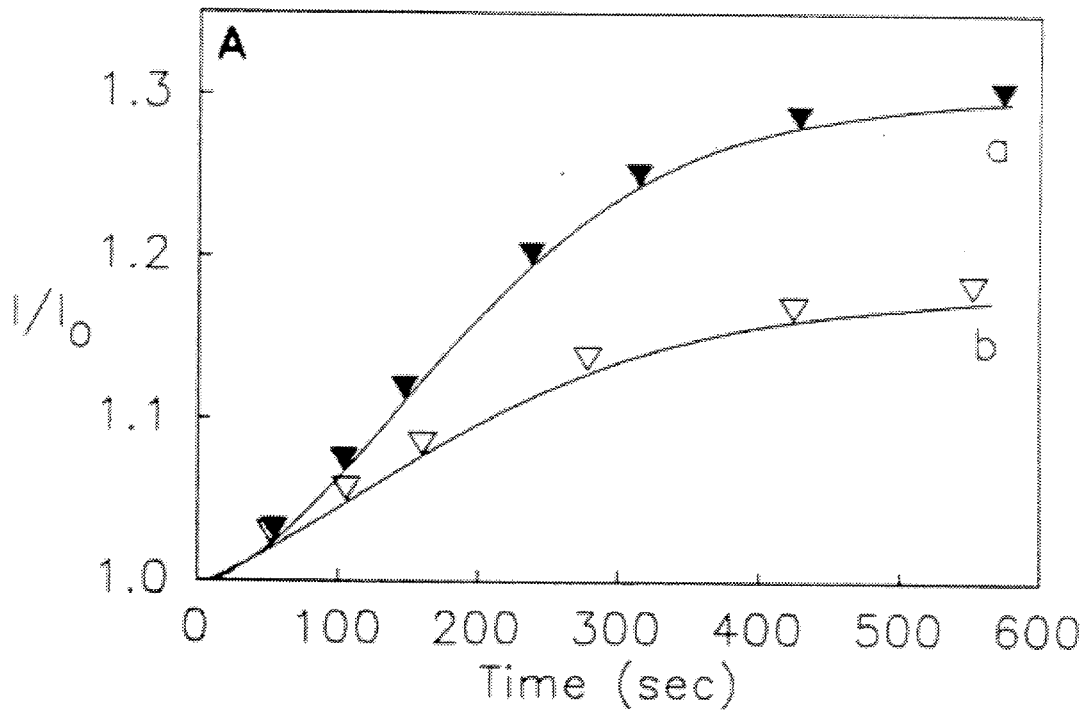
FIG. 7A
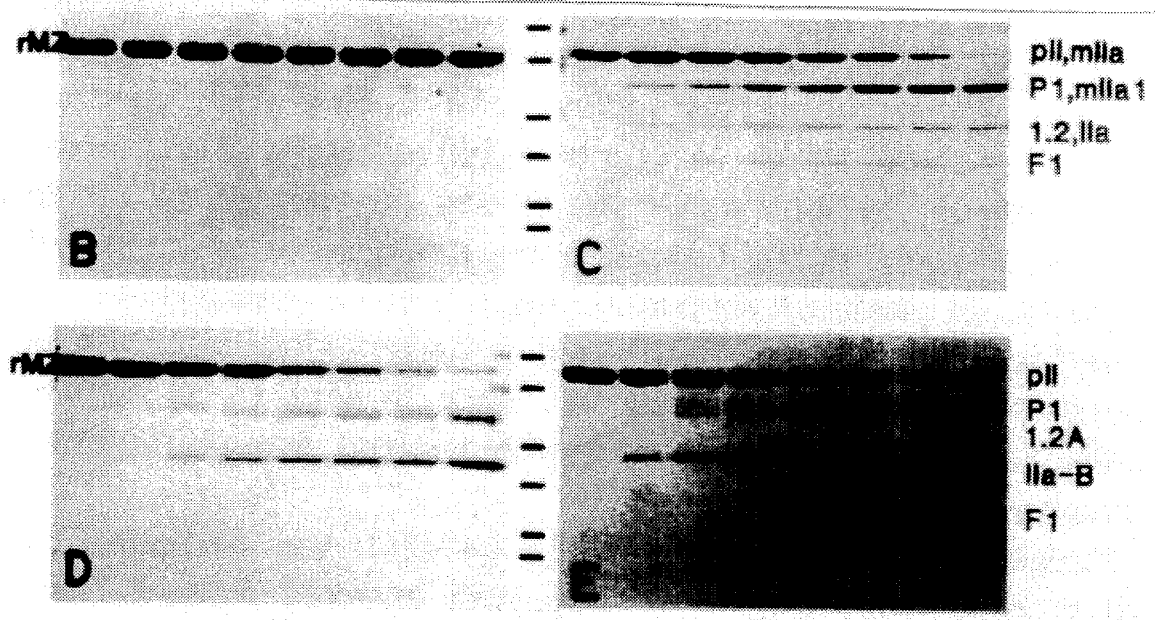
FIG. 7B  FIG. 7C
FIG. 7D  FIG. 7E

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: 5'end modification ( i x ) FEATURE:
        ( A ) NAME/KEY: CDS
        ( B ) LOCATION: 1..29

( x i ) SEQUENCE DESCRIPTION: SEQ ID NO:1:

ACACCCGGGC AGGAGCTGAC ACACTATGG 29

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: 5'end modification ( i x ) FEATURE:
        ( A ) NAME/KEY: CDS
        ( B ) LOCATION: 1..20

( x i ) SEQUENCE DESCRIPTION: SEQ ID NO:2:

GCAGCAAGCT TATCTCGAGG 20

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: DNA (genomic)

( v i i ) IMMEDIATE SOURCE:
        ( B ) CLONE: 3'end modification ( x i ) SEQUENCE DESCRIPTION: SEQ ID NO:3:

ACATCTAGAC GCTGAGAGTC ACTTTTATT 29

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

(vii) IMMEDIATE SOURCE:
(B) CLONE: 3'end modification (ix) FEATURE:
(A) NAME/KEY: CDS
(B) LOCATION: 1..20

(xi) SEQUENCE DESCRIPTION: SEQ ID NO:4:

AGTGTCCTGC AGGTGGTGAA 20

(2) INFORMATION FOR SEQ ID NO:5:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: R155A (ix) FEATURE:
(A) NAME/KEY: CDS
(B) LOCATION: 1..22

(xi) SEQUENCE DESCRIPTION: SEQ ID NO:5:

GATGACTCCA GCCTCCGAAG GC 22

(2) INFORMATION FOR SEQ ID NO:6:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(A) LIBRARY: R271A (ix) FEATURE:
(A) NAME/KEY: CDS
(B) LOCATION: 1..22

(xi) SEQUENCE DESCRIPTION: SEQ ID NO:6:

CATCGAAGGG GCTACCGCCA CA 22

(2) INFORMATION FOR SEQ ID NO:7:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: DNA (genomic)

(vii) IMMEDIATE SOURCE:
(B) CLONE: R284A (ix) FEATURE:
(A) NAME/KEY: CDS
(B) LOCATION: 1..22

(xi) SEQUENCE DESCRIPTION: SEQ ID NO:7:

CAATCCGGCG ACCTTTGGCT CG 22

(2) INFORMATION FOR SEQ ID NO:8:

-continued ( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA (genomic)

( v i i ) IMMEDIATE SOURCE:
( B ) CLONE: sequencing primer ( i x ) FEATURE:
( A ) NAME/KEY: CDS
( B ) LOCATION: 1..20

( x i ) SEQUENCE DESCRIPTION: SEQ ID NO:8:

ACTATAAAGA GGGCAGGCTG 20

STABLE RECOMBINANT MEIZOTHROMBIN-LIKE POLYPEPTIDES

BACKGROUND OF THE INVENTION

1. Field of the Invention

This invention relates generally to the field of blood coagulation and specifically to new stable recombinant meizothrombin-like molecules which have anti-coagulant activity.

2. Description of Related Art

During the final stages of blood coagulation, prothrombin is converted from an inactive zymogen to the serine protease thrombin, an enzyme which plays a central role in hemostasis. Prothrombin is synthesized in the liver and undergoes several post-translational modifications prior to secretion. These modifications include glycosylation, cleavage of the pre- and pro-peptides and vitamin K-dependent γ-carboxylation of the first 10 amino terminal glutamic acid residues. The γ-carboxyglutamic acid (Gla) residues are involved in the metal ion-dependent interaction of prothrombin with phospholipid surfaces. Activation of prothrombin to thrombin results from the proteolytic cleavage of $Arg^{271}$—$Thr^{272}$ and $Arg^{320}$—$Ile^{321}$ by factor Xa. Although factor Xa alone will catalyze the activation of prothrombin slowly, the reaction progresses five orders of magnitude more rapidly in the presence of the prothrombinase complex, which consists of factor Xa, the cofactor factor Va, calcium ions and a negatively charged phospholipid surface.

Depending on the order of peptide bond cleavage, two intermediate products, meizothrombin and prethrombin-2, can exist in the reaction pathway (See FIG. 1). Meizothrombin is produced by proteolytic cleavage of the $Arg^{320}$—$Ile^{321}$ bond by factor Xa yielding fragment 1.2-thrombin A chain joined to the thrombin B chain by a disulfide bond. Meizothrombin is capable of catalyzing the cleavage of the $Arg^{155}$—$Ser^{156}$ bond which releases the fragment 1 (F1) domain and yields an active species called meizothrombin (desF1), which no longer contains the γ-carboxylated (Gla) region and exhibits functional activities different from those of meizothrombin. The pair, fragment 1.2 plus prethrombin-2, results from the cleavage of the $Arg^{271}$—$Thr^{272}$ bond. Although prethrombin-2, with the exception of the bond at $Arg^{320}$—$Ile^{321}$, is identical in covalent structure to thrombin, it has no proteolytic activity.

The existence of meizothrombin as an intermediate in the prothrombinase-catalyzed activation of prothrombin was described by Rosing, et al., (J. Biol. Chem. 261:4224, 1986). Further studies indicated that it appears to be the main, if not sole intermediate of the activation of prothrombin by the fully assembled prothrombinase complex in vitro. Human thrombin formed on the surface of endothelial cells influences the formation of meizothrombin via a feedback mechanism, leading to the accumulation of meizothrombin (desF1) in the final phase of prothrombin activation. The specific role of factor Va in meizothrombin formation has not been clarified to date. Factor Va, however, interacts with both factor Xa and prothrombin and presents them to one another in the formation of a ternary enzyme-substrate-cofactor complex (Boskovic, et al., J. Biol. Chem. 265:10497, 1990). In addition, if factor Va is omitted from the reaction, prethrombin-2 is the main intermediate observed.

Studies of human meizothrombin have been hampered by its extremely transient existence due to autolysis that results in rapid formation of meizothrombin (desF1), and further rapid activation to α-thrombin. Furthermore, electrophoretic analysis under non-reducing conditions is complicated because meizothrombin and meizothrombin (desF1) have molecular weights that are identical to those of prothrombin and prethrombin-1. Reversible thrombin inhibitors allow the isolation of meizothrombin, but make subsequent enzymatic characterization difficult. Even in the presence of the reversible inhibitor dansylarginine N-(3-ethyl-1,5 pentanediyl) amide (DAPA), the meizothrombin generated is only stable for a few hours on ice before autolysis occurs and meizothrombin (desF1) appears.

The study of the role of native meizothrombin in thrombosis and hemostasis disorders has been severely hampered by its unstable nature. For example, two congenital dysprothrombinemia cases have been described, prothrombin Barcelona and prothrombin Madrid. In both cases, the defect is characterized by a very low thrombin generation and coagulant activity, but normal prothrombin antigen level. The molecular defect in both families is due to the substitution of $Arg^{271}$ to Cys which disrupts one of the two factor Xa cleavage sites and alters the activation of the molecule. Exposure of prothrombin Barcelona and Madrid to factor Xa results in cleavage of the $Arg^{320}$—$Ile^{321}$ bond, yielding meizothrombin. This mutant prothrombin appears to offer a model to study the activity of meizothrombin, but since the thrombin cleavage sites are intact, generation of meizothrombin (desF1) and α-thrombin (desA 1–13) would probably occur and complicate the analysis. In addition, the new cysteine residue could also form an abnormal disulfide bond and affect the folding of the protein.

Presently, one of the most common anticoagulant used in patients is heparin. Heparin acts as an anticoagulant by a heparin-antithrombin interaction, which induces a conformational change in antithrombin III (ATIII) that is responsible for acceleration of inactivation of clotting enzymes. Heparin is a heterogeneous mixture of sulfated polysaccharide chains ranging in molecular weight from 5000–35000 daltons. Many studies have shown that the low molecular weight fraction (LMW) of heparin is less hemorrhagic than unfractionated heparin (UF) (Esquivel, et al., Thromb. Res. 28:389, 1982; Carter, et al., Blood 59:1239, 1982). However, other studies have found that for equivalent antithrombin doses, some LMW fractions have the same hemorrhagic effect as UF heparin (Diness, et al., Thromb. Haemost. 55:410, 1986).

Thus, there exists a need for a anticoagulant agent which inhibits coagulation with greater specificity and without the degree of hemorrhagic side effects of heparin. It would be especially valuable if such anticoagulant agent could be used in clinical settings where the thrombosis process is unresponsive to heparin treatment. The apparently unique functional properties of native meizothrombin and the difficulties associated with this transient prothrombin activation intermediate motivated the investigation for a more stable form of the protein. The present invention fulfills a longfelt need for a safe, stable meizothrombin-like anticoagulant molecule.

SUMMARY OF THE INVENTION

The present invention provides a novel recombinant meizothrombin polypeptide (rhMZ) which is characterized by having anticoagulant activity and having the amino acid sequence of prothrombin with amino acid substitutions at residues 155, 271 and 284. Preferably, the arginine residues normally found at these positions are replaced by alanine.

Unlike native meizothrombin, the resulting meizothrombin-like molecule is highly stable. This stability is achieved by amino acid substitutions that disrupt two thrombin and one factor Xa cleavage sites so that they are no longer recognized by the specific proteases. The invention also provides a second meizothrombin-like polypeptide which contains a fourth amino acid substitution at position 320 (rhQM), which renders the protein resistant to activation.

The invention also provides a method for producing the tri-substituted polypeptide (rhMZ), which, upon activation, stimulates production of activated protein C, and a method for producing the tetra-substituted polypeptide (rhQM), which acts as a prothrombin molecule and is incapable of activation.

In another embodiment, the present invention provides a method of inhibiting coagulation in a subject who has or is at risk of having arterial thrombosis, by administering the polypeptide(s) of the invention.

BRIEF DESCRIPTION OF THE DRAWINGS

FIGS. 6A–6E show prothrombinase-catalyzed activation of prothrombin (pII) and rMZ(I) monitored by fluorescence changes in the presence of DAPA (A) and SDS-PAGE (B–E).

FIGS. 7A–7E show prothrombinase-catalyzed activation of prothrombin (pII) and rMZ(I) monitored by intrinsic fluorescence (A) and SDS-PAGE (B–E).

DETAILED DESCRIPTION OF THE INVENTION

Figure 1:
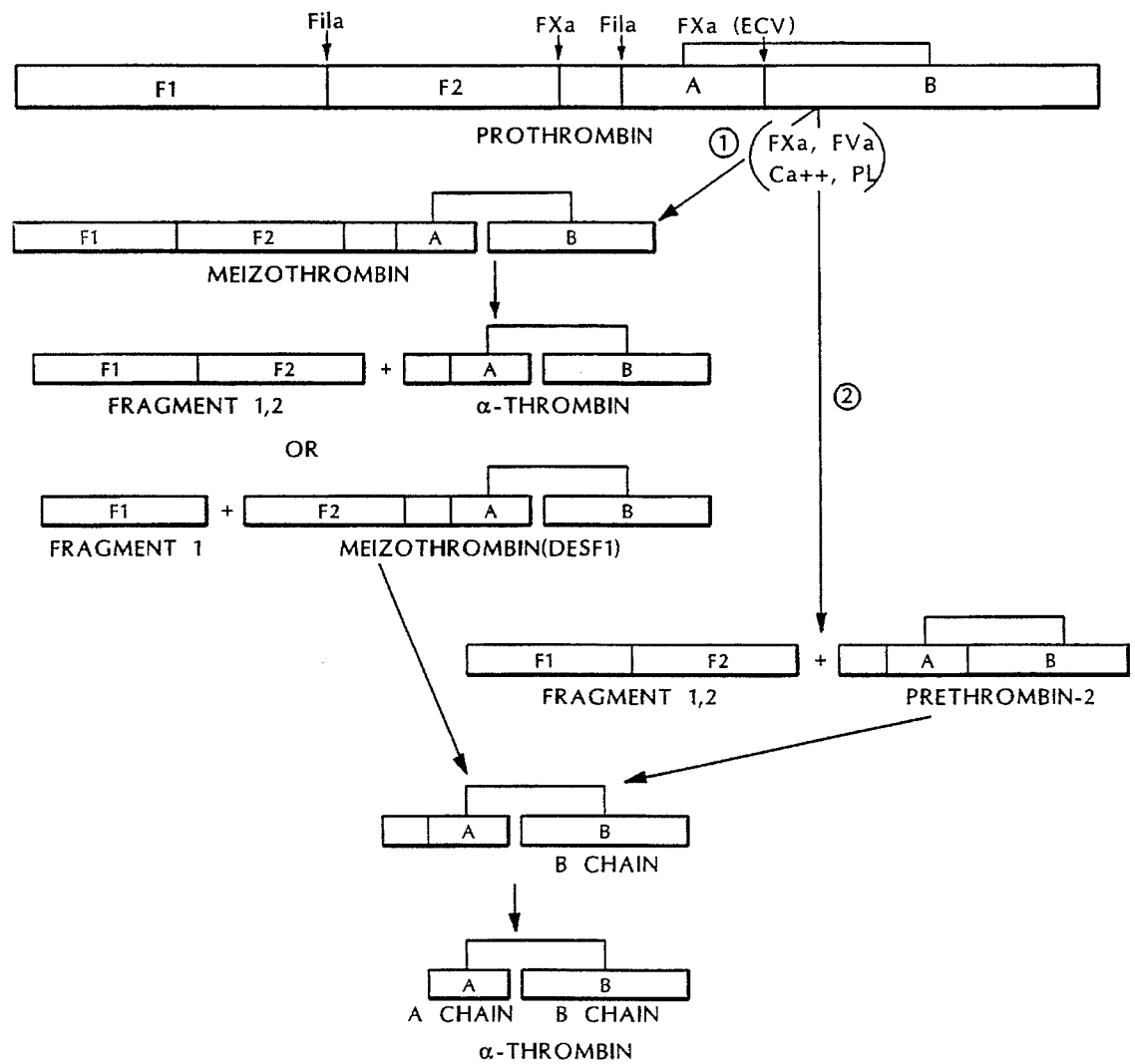
FIG. 1 is a diagram of the prothrombin activation pathways.

The present invention provides two novel meizothrombin-like molecules with anti-coagulant activity. Both polypeptides have the amino acid sequence of prothrombin with amino acid substitutions at residues 155, 271, and 284. One polypeptide has an additional amino acid substitution at residue 320.

The first polypeptide of the invention contains three amino acid substitutions in the human prothrombin sequence and is referred to as rhMZ, or recombinant human meizothrombin. The amino acid substitutions are at arginine residues located at positions 155, 271 and 284. These mutations disrupt two thrombin and one factor Xa cleavage sites so that they are not recognized by the specific proteases. These mutations alter the activity of the activated molecule (rhMZa) in that it greatly reduces its procoagulant activity toward fibrinogen (to about 7% of that of prothrombin), but does not alter its anticoagulant activity toward protein C. Protein C, once activated (APC), acts as an anticoagulant by inactivating Factor VIIIa (FVIIIa) and Factor Va (FVa), two cofactors required for efficient coagulation in vivo. rhMZ can be activated by the snake venom activator ecarin or by naturally occurring prothrombinase complex, which hydrolyses the peptide bond $Arg^{320}$—$Ile^{321}$ to produce rhMZa, an active serine protease. rhMZa has the ability to activate protein C to APC, thereby inhibiting coagulation and stimulating APC's fibrinolytic activity. Unlike native meizothrombin, rhMZ and rhMZa are extremely stable molecules.

The second polypeptide of the invention contains not only the amino acid substitutions as described above for rhMZ, but also contains an additional substitution at amino acid residue 320. This polypeptide is referred to as rhQM, or recombinant human quadruple mutant prothrombin. The four mutations in rhQM disrupt all of the proteolytic cleavage sites in the protein and renders rhQM resistant to activation. Because rhQM mimics inactive prothrombin, rhQM acts as a reversible dose-dependent inhibitor of coagulation by competing for interaction with Factor Xa and Factor Va on the phospholipid surface.

Administration of the rhMZ and/or rhQM polypeptides of the invention, alone or in combination with other thrombolytic or fibrinolytic agents, is useful in various clinical situations. These include: 1) acute arterial thrombotic occlusion including coronary, cerebral or peripheral arteries; 2) acute thrombotic occlusion or restenosis after angioplasty; 3) reocclusion or restenosis after thrombolytic therapy (e.g., in an ishemic tissue); 4) vascular graft occlusion; 5) hemodialysis; 6) cardiopulmonary bypass surgery; 7) left ventricular cardiac assist device; 8) total artificial heart and left ventricular assist devices; 9) septic shock; and 10) other arterial thromboses (e.g., thrombosis or thromboembolism where current therapeutic measures are either contraindicated or not effective).

The polypeptides of the invention are a derivative of a naturally occurring physiologic human protein. Due to their specificity of action and dosage requirements, the polypeptides of the invention are superior to other available antithrombotic agents in terms of bleeding tendency (heparin, antiplatelet drugs), toxicity, antigenicity (streptokinase), clearance rate (heparin), teratogenicity (coumarin derivatives), general side effects (antiplatelet drugs), lack of immediate efficacy (antiplatelet drugs, coumarin derivatives), allergic reactions (antiplatelet drugs, streptokinase, heparin) and hypotensive effect (prostacyclin).

Amino acid substitutions in the recombinant meizothrombin molecule of the invention occur at specific proteolytic cleavage sites. Arginine residues preceding the normally hydrolyzed peptide bonds are substituted with another amino acid. Preferably, the substituted amino acid is a small, neutral amino acid, however, any other amino acid which would not disrupt the function of the molecule and would not allow the cleavage sites to be recognized by the specific proteases can be substituted for arginine. As noted, the preferred substituted amino acid is a small, neutral amino acid such as alanine, glycine, leucine, isoleucine, serine, threonine, valine and methionine. Also included are synthetic amino acids which are chemically produced or modified and are capable of inhibiting proteolytic cleavage at the sites described.

Minor modifications of the primary amino acid sequence of the polypeptides of the invention may result in polypeptides which have substantially equivalent activity as compared to the specific polypeptides described herein. Such modifications may be deliberate, as by site-directed mutagenesis, or may be spontaneous. All of the polypeptides produced by these modifications are included herein as long as the biological activity of the original peptide still exists. For example, a modified polypeptide must still contain the cleavage sites which cannot be recognized by the specific protease. Further, deletion of one or more amino acids can also result in a modification of the structure of the resultant molecule without significantly altering its biological activity. This can lead to the development of a smaller active molecule which would also have utility. For example, it may be possible to remove amino or carboxy terminal amino acids which may not be required for biological activity of the particular polypeptide.

In addition to the four discrete proteolytic sites described above, the invention embraces conservative variations in the remaining amino acid sequence of the polypeptide of the invention. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term does not refer to the four specific cleavage sites indicated, where the amino acid substitutions are limited to those small, neutral amino acids described above.

The invention also provides polynucleotides which encode the polypeptides of the invention. As used herein, "polynucleotide" refers to a polymer of deoxyribonucleotides or ribonucleotides, in the form of a separate fragment or as a component of a larger construct. DNA encoding a peptide of the invention can be assembled from cDNA fragments or from oligonucleotides which provide a synthetic gene which is capable of being expressed in a recombinant transcriptional unit. Polynucleotide sequences of the invention include DNA, RNA and cDNA sequences. A polynucleotide sequence can be deduced from the genetic code, however, the degeneracy of the code must be taken into account. Polynucleotides of the invention include sequences which are degenerate as a result of the genetic code.

A nucleotide sequence which encodes prothrombin can be isolated using several methods described herein, and the appropriate areinc acid substitutions can then be made by mutagenesis techniques commonly known in the art. For example, the amino acid substitutions can be made using the dut⁻ ung⁻ technique of Kunkel, et al.,(Proc. Natl. Acad. Sci., U.S.A., 82:488, 1985) oligonucleotide-directed mutagenesis, region-specific mutagenesis, linker-scanning mutagenesis, or oligonucleotide-directed mutagenesis that utilizes the polymerase chain reaction (PCR) (See Ausubel, et al., Current Protocols in Molecular Biology, Wiley Interscience, 1989, Unit 8).

DNA sequences of the invention can be obtained by several methods. For example, the DNA can be isolated using hybridization procedures which are well known in the art. These include, but are not limited to: 1) hybridization of probes to genomic or cDNA libraries to detect shared nucleotide sequences; antibody screening of expression libraries to detect shared structural features and 3) synthesis by the polymerase chain reaction (PCR).

Hybridization procedures are useful for the screening of recombinant clones by using labeled mixed synthetic oligonucleotide probes where each probe is potentially the complete complement of a specific DNA sequence in the hybridization sample which includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al, Nucleic Acid Research, 9:879, 1981).

Screening procedures which rely on nucleic acid hybridization make it possible to isolate any gene sequence from any organism, provided the appropriate probe is available. Oligonucleotide probes, which correspond to a part of the sequence encoding the protein in question, can be synthesized chemically. This requires that short, oligopeptide stretches of amino acid sequence must be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture which is its complete complement (Wallace, et al., Nucl. Acid Res., 9:879, 1981).

The development of specific DNA sequences encoding prothrombin can also be obtained by: 1) isolation of double-stranded DNA sequences from the genomic DNA; 2) chemical manufacture of a DNA sequence to provide the necessary codons for the polypeptide of interest; and 3) in vitro synthesis of a double-stranded DNA sequence by reverse transcription of mRNA isolated from a eukaryotic donor cell. In the latter case, a double-stranded DNA complement of mRNA is eventually formed which is generally referred to as cDNA. Of these three methods for developing specific DNA sequences for use in recombinant procedures, the isolation of genomic DNA isolates is the least common. This is especially true when it is desirable to obtain the microbial expression of mammalian polypeptides due to the presence of introns.

The synthesis of DNA sequences is frequently the method of choice when the entire sequence of amino acid residues of the desired polypeptide product is known. When the entire sequence of amino acid residues of the desired polypeptide is not known, the direct synthesis of DNA sequences is not possible and the method of choice is the synthesis of cDNA sequences. Among the standard procedures for isolating cDNA sequences of interest is the formation of plasmid- or phage-carrying cDNA libraries which are derived from reverse transcription of mRNA which is abundant in donor cells that have a high level of genetic expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA may be employed in DNA/DNA hybridization procedures which are carried out on cloned copies of the cDNA which have been denatured into a single-stranded form (Jay et al., Nucl. Acid Res. 11:2325, 1983).

A cDNA expression library, such as lambda gt11, can be screened indirectly for prothrombin polypeptide having at least one epitope, using antibodies specific for prothrombin. Such antibodies can be either polyclonally or monoclonally derived and used to detect expression product indicative of the presence of prothrombin cDNA.

Polynucleotide sequences encoding the polypeptides of the invention can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

The polynucleotide sequence encoding the polypeptide of the invention can be derived from bovine, porcine or human, for example. Preferably, the polynucleotide of the invention is human. Any source of prothrombin nucleotide sequence is included, as long as the substitutions at the proteolytic cleavage sites result in the inability of the protein to be activated, as described for the rhMZ and rhQM of the invention.

DNA sequences encoding the polypeptides can be expressed in vitro by DNA transfer into a suitable host cell. "Host cells" are cells in which a vector can be propagated and its DNA expressed. The term also includes any progeny of the subject host cell. It is understood that all progeny may not be identical to the parental cell since there may be mutations that occur during replication. However, such progeny are included when the term "host cell" is used. Methods of stable transfer, in other words when the foreign DNA is continuously maintained in the host, are known in the art.

In the present invention, the rhMZ or rhQM polynucleotide sequences may be inserted into a recombinant expression vector. The term "recombinant expression vector" refers to a plasmid, virus or other vehicle known in the art that has been manipulated by insertion or incorporation of the genetic sequences. Such expression vectors contain a promoter sequence which facilitates the efficient transcription of the inserted genetic sequence of the host. The expression vector typically contains an origin of replication, a promoter, as well as specific genes which allow phenotypic selection of the transformed cells. Vectors suitable for use in the present invention include, but are not limited to the T7-based expression vector for expression in bacteria (Rosenberg et al., Gene 56:125, 1987), the pMSXND expression vector for expression in mammalian cells (Lee and Nathans, J. Biol. Chem. 263:3521, 1988) and baculovirus-derived vectors for expression in insect cells. The DNA segment can be present in the vector operably linked to regulatory elements, for example, a promoter (e.g., T7, metallothionein I, or polyhedrin promoters).

The vector may include a phenotypically selectable marker to identify host cells which contain the expression vector. Examples of such markers typically used in mammalian expression vectors include the gene for adenosine deaminase (ADA), aminoglycoside phosphotransferase (neo, G418), dihydrofolate reductase (DHFR), hygromycin-B-phosphotransferase (HPH), thymidine kinase (TK), and xanthine guanine phosphoribosyltransferse (XGPRT, gpt).

Transformation of a host cell with recombinant DNA may be carried out by conventional techniques which are well known to those skilled in the art. Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the polypeptides of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Examples of mammalian host cells include COS, BHK, 293, HepG2, CV-1, and CHO cells.

Isolation and purification of host cell expressed polypeptide, or fragments thereof, provided by the invention, may be carried out by conventional means including preparative chromatography and immunological separations involving monoclonal or polyclonal antibodies.

Antibodies provided in the present invention are immunoreactive or bind to rhMZ or rhQM. Antibody which consists essentially of pooled monoclonal antibodies with different epitopic specificities, as well as distinct monoclonal antibody preparations are provided. Monoclonal antibodies are made from antigen containing fragments of the protein by methods well known in the art (Kohler, et al., Nature, 256:495, 1975; Current Protocols in Molecular Biology, Ausubel, et al., ed., 1989).

Antibodies which specifically bind to the polypeptides of the invention, but not to prothrombin, can be prepared using an intact polypeptide (rhMZ or rhQM) or fragments containing the amino acid substitutions as the immunizing antigen. A peptide used to immunize an animal can be derived from translated cDNA or chemical synthesis and is purified and conjugated to a carrier protein, if desired. Such commonly used carriers which are chemically coupled to the peptide include keyhole limpet hemocyanin (KLH), thyroglobulin, bovine serum albumin (BSA), and tetanus toxoid. The coupled peptide is then used to immunize the animal (e.g., a mouse or a rabbit).

The production of polyclonal and monoclonal antibodies is routine using the current techniques available. Screening techniques allow identification of antibodies which react with the polypeptides of the invention, but not prothrombin. For example, a sample containing antibodies prepared against a polypeptide of the invention is passed over a column with prothrombin bound to it, in order to eliminate any prothrombin-binding antibodies. The flow through is then passed over a column containing the rhMZ or rhQM polypeptides of the invention and any antibody which binds is rhMZ- or rhQM-specific.

The invention also provides a method for producing a polypeptide, which, upon activation, stimulates production of activated protein C. The method includes the steps of introducing into a host cell an expression vector which contains a nucleotide sequence which encodes a polypeptide, which, upon activation, stimulates production of activated protein C; culturing the host cell in an appropriate medium; and isolating the polypeptide product encoded by the expression vector. Preferably, the polypeptide has the activity of the rhMZ polypeptide of the invention.

The method for producing a polypeptide such as rhMZ further includes cleaving the polypeptide with a protease. For example, the snake venom activator ecarin, which hydrolyzes the bond between $Arg^{320}$—$Ile^{321}$, can be used. Alternatively, the naturally occurring prothrombinase complex and components thereof (e.g., factor Xa and Va) can also be used to activate the polypeptide. Other methods known to those of skill in the art can also be used to activate rhMZ. Preferably, the polypeptide is activated/n vitro or in vivo prior to administration to a subject.

The invention also provides a method for producing a polypeptide which acts as a prothrombin molecule which cannot be activated. The method includes the steps of introducing into a host cell an expression vector which contains a nucleotide sequence which encodes a polypeptide which acts as an inactive prothrombin molecule and is incapable of activation; culturing the host cell in an appropriate medium; and isolating the polypeptide product encoded by the expression vector. Preferably, the polypeptide is the rhQM of the invention.

The invention also provides a method for ameliorating thrombosis in a subject having or at risk of having arterial thrombosis comprising administering a therapeutically effective amount of the polypeptide(s) of the invention. As used herein, the term "ameliorate" denotes a lessening of the detrimental effects of a thrombosis in the subject receiving therapy. The term "therapeutically effective" means that the amount of polypeptide used is of sufficient quantity to ameliorate the effects of the thrombosis.

The polypeptides of the invention can be administered parenterally by injection or by gradual infusion over time. The polypeptides can be administered intravenously, intraperitoneally, intramuscularly, subcutaneously, intracavity, or transdermally. As described above, it is preferable to activate rhMZ prior to administration to the subject.

Preparations for parenteral administration of a the anticoagulant polypeptides of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Using the polypeptides in the therapeutic method of the invention, it is possible to design therapies combining all of the characteristics described herein. For example, in a given situation, it may be desirable to administer a therapeutic agent, or agents, prior to the administration of the polypeptides of the invention. Those of skill in the therapeutic art can readily establish the appropriate dose of polypeptide of the invention in a given situation by considering such factors as the age, sex, clotting time, and related patient factors without undue experimentation.

The polypeptides of the invention can be administered alone or in combination with each other or with another thrombolytic or fibrinolytic agent. Such agents include tissue plasminogen activator, urokinase, prourokinase, heparin, and streptokinase, for example. Administration of rhMZ with tissue plasminogen activator for example, would reduce the dose of tissue plasminogen activator that would be required, thereby reducing the risk of clot formation which is often associated with the conclusion of tissue plasminogen activator and other thrombolytic or fibrinolytic therapies.

The following examples are intended to illustrate but not limit the invention. While they are typical of those that might be used, other procedures known to those skilled in the art may alternatively be used.

EXAMPLE 1

Material and Methods

Materials—Dulbecco's modified Eagle medium; Nutrient Mixture F-12 (ham) (1:1) powder and new-born calf serum were purchased from Gibco (Grand Island, N.Y.). Low protein serum replacement (LPSR-1) was from Sigma Chemical Co. (St. Louis, Mo.). Methotrexate sodium injection (David Bull Laboratories, Mulgrave, Victoria, Australia) and vitamin $K_1$ (Sabex, Boucherville, Quebec) were purchased at the local hospital pharmacy. Sheep anti-human prothrombin was from Affinity Biologicals (Yarker, Ontario) and anti-sheet IgG alkaline phosphatase was from Chemicon (Temecula, Calif.). The BHK cell line and pNUT vector were from Dr. Richard Palmiter (Howard Hughes Medical Institute, University of Washington), and S-2238 (D-phenylalanyl-L-pipecolyl-L-arginine-p-nitroanilide-dihydrochloride) was from Helena Laboratories (Mississauga, Ontario). Phospholipid vesicles (75% PC/25% PS) were prepared as described by Bloom, et al., (Biochemistry, 18:4419–4425, 1979). Factor X (Krishnaswamy, S., et al., J. Biol. Chem., 262L:3281–3299, 1987) and factor V (Nesheim, M. E., et al., Methods in Enzymol., 80:249–274, 1981) were isolated and activated as described previously. The prothrombin activator of Echis arinatus venom (Sigma) was isolated by anion-exchange chromatography and preparative electrophoresis in polyacrylamide as described previously (Boskovic, D. S. et al. J. Biol. Chem., 265:10497–10505, 1990).

Figure 2:
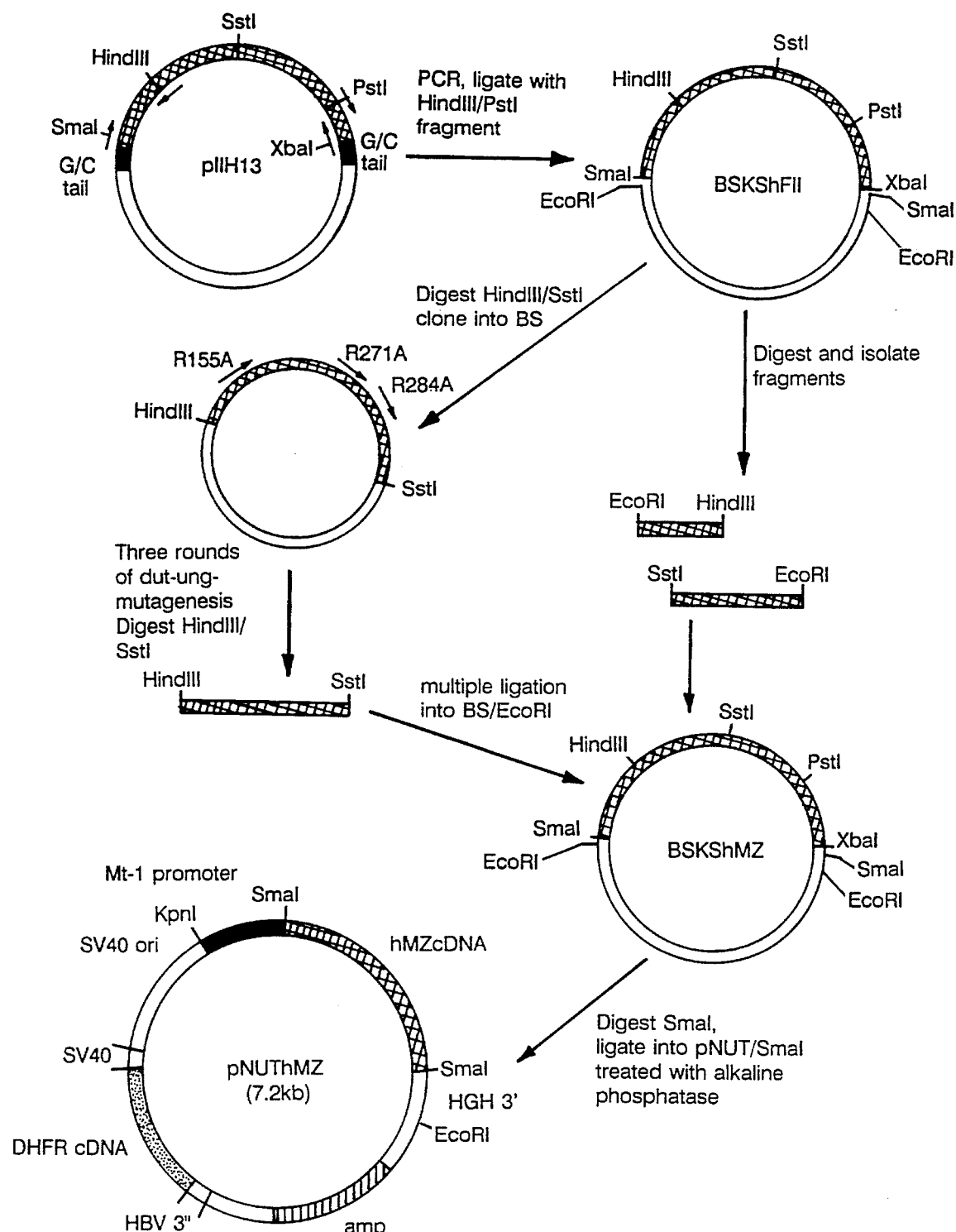
FIG. 2 shows the construction of the hMZ expression vector in pNUT.

DNA Construction and Mutagenesis: The plasmid pIIH13 containing the full-length human prothrombin cDNA (MacGillivray, R. T. A., et al., Ann. N Y Acad. Sci., 485:73–79, 1986; Degen, et al., Biochemistry 22:2087–2097, 1983) was modified using the polymerase chain reaction (PCR) to eliminate the dG/dC tails. The 5' and 3' ends of the cDNA were subjected to PCR with oligonucleotides 1–2 and 3–4 (Table I) respectively. The resulting Sma I-Hind III and Pst I-Xba I fragments were ligated with the central Hind III-Pst I portion from the original plasmid pIIH13 into Bluescript to generate phFII containing the wild type human prothrombin cDNA. In order to prepare the meizothrombin variant, a 700 bp Hind III-Sst I fragment was subcloned into Bluescript and the three mutations R155A, R271A and R284A were introduced by using the dut⁻ ung⁻ mutagenesis technique (Kunkel, T. A., Proc. Natl. Acad. Sci., U.S.A., 82:488–492, 1985) with oligonucleotides 5,6, and 7 respectively. The triple mutant HindIII-Sst I fragment was then ligated back into phFII to create phMZ (FIG. 2). The presence of the mutations was verified by DNA sequence analysis using the chain termination method.

For expression in mammalian cells, the hMZ cDNA was ligated into the pNUT (FIG. 2) vector which encodes a modified dihydrofolate reductase gene (driven by the early SV40 promoter) and allows selection under high methotrexate (MTX) concentration. The cDNA was inserted into the Sma I site downstream of the zinc-inducible mouse metallothionein 1 promoter and upstream of the human growth hormone polyadenylation signal. Proper orientation of the construct was confirmed by using PCR with oligonucleotides 2 and 8, restriction endonuclease analysis, and DNA sequence analysis.

TABLE I

OLIGONUCLEOTIDES FOR PCR

| # | Sequence | Use |
|---|----------|-----|
| 1 | 5' ACACCCGGGCAGGAGCTGACACACTATGG 3' | 5' end modification |
| 2 | 5' GCAGCAAGCTTATCTCGAGG 3' | 5' end modification |
| 3 | 5' ACATCTAGACGCTGAGAGTCACTTTTATT 3' | 3' end modification |
| 4 | 5' AGTGTCCTGCAGGTGGTGAA 3' | 3' end modification |
| 5 | 5' GATGACTCCAGCCTCCGAAGGC 3' | R155A |
| 6 | 5' CATCGAAGGGGCTACCGCCACA 3' | R271A |
| 7 | 5' CAATCCGGCGACCTTTGGCTCG 3' | R284A |
| 8 | 5' ACTATAAAGAGGGCAGGCTG 3' | sequencing primer |

Cell Culture, Transfection, Selection—Baby hamster kidney cells (BHK) were cultured in Dulbecco's modified Eagle's medium; nutrient mixture F-12 (1:1) (DMEM-F12) supplemented with 5% new-born calf serum during transfection and selection. The cells were transfected by the calcium-phosphate co-precipitation technique (Searle, P. F., et al., Mol. Cell. Biol., 5:1480–1489, 1985). The DNA (20 µg) was precipitated at pH 6.95 and added to the cells for 5 to 7 hours. After 12 hours, the medium was changed to DMEM-F12/5% new-born calf serum containing 0.44 mM methotrexate (MTX). After approximately 12 days of selection, drug-resistant colonies were isolated by trypsin treatment (0.25% trypsin), performed at the tip of a transfer pipet, and were cultured in six well plates. The cloned cells were then grown to confluence in low protein serum replacement medium and levels of expression were evaluated by Western blot analysis and ELISA with sheep anti-human prothrombin antibody. The highest secreting clone was seeded into roller bottles. For large scale expression, the cells were cultured in DMEM-F12, 1% LPSR, and 10.0 µg/mL vitamin $K_1$. The medium was collected every two to three days during the first three weeks and everyday subsequently. The collected samples were stored at 4° C. until used.

EXAMPLE 2

Expression of Recombinant Meizothrombin

The expression of wild type recombinant human prothrombin using pNUT and BHK cells has been described in detail (Le Bonniec, B. F., et al., J. Biol. Chem., 266:13796–13803, 1991). By removing the poly G:C tails in the cDNA, by using higher levels of methotrexate during initial selection of transfectants, and by culturing in roller bottles with serum-free medium, BHK cell lines have been obtained that express much higher levels of recombinant prothrombin than those reported previously (Jorgensen, M. J., et al., J. Biol. Chem., 262:1–6, 1987; Le Bonniec, B. F., et al., J. Biol. Chem., 266:13796–13803, 1991; Falkner, F. G., et al., Thromb. Haemostasis, 2:119–124, 1992). One such cell line secreted approximately 200 µg/mL of recombinant prothrombin into the medium. Upon activation of the purified recombinant prothrombin with the prothrombinase complex, however, incomplete activation was observed, consistent with under γ-carboxylation of the recombinant protein. This apparent saturation of the carboxylation machinery in BHK cells producing high levels of recombinant vitamin K-dependent protein has been reported previously (Bushy, S., et al., Nature, 316:271–273, 1985).

Figure 3A:
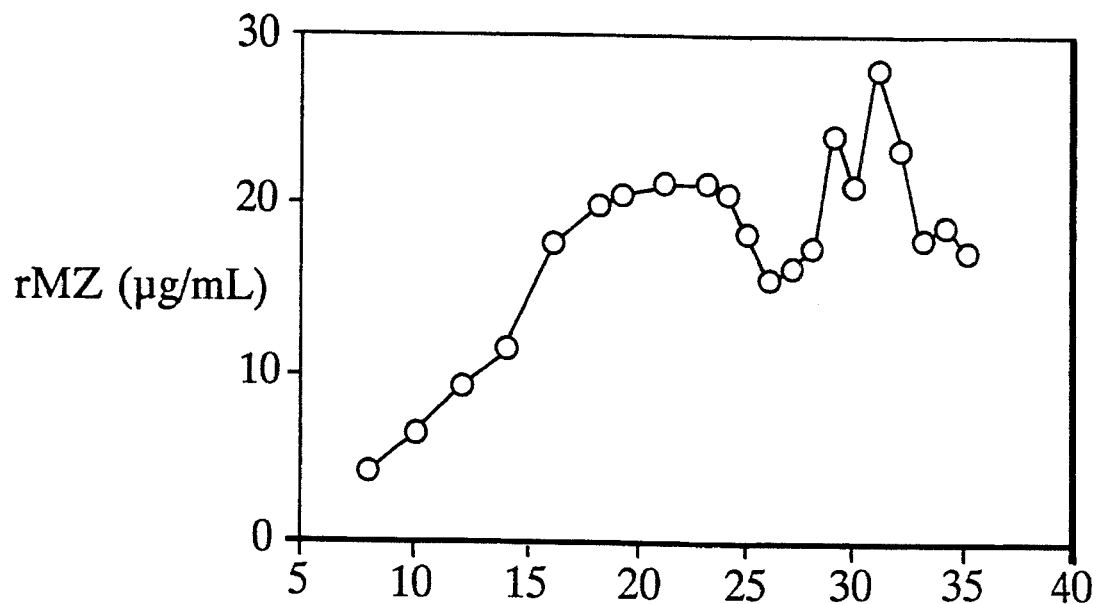
FIGS. 3(A and B) show the production rate (A) and cumulative yield (B) of rMZ produced by BHK cells cultured in a roller bottle.
Figure 3B:
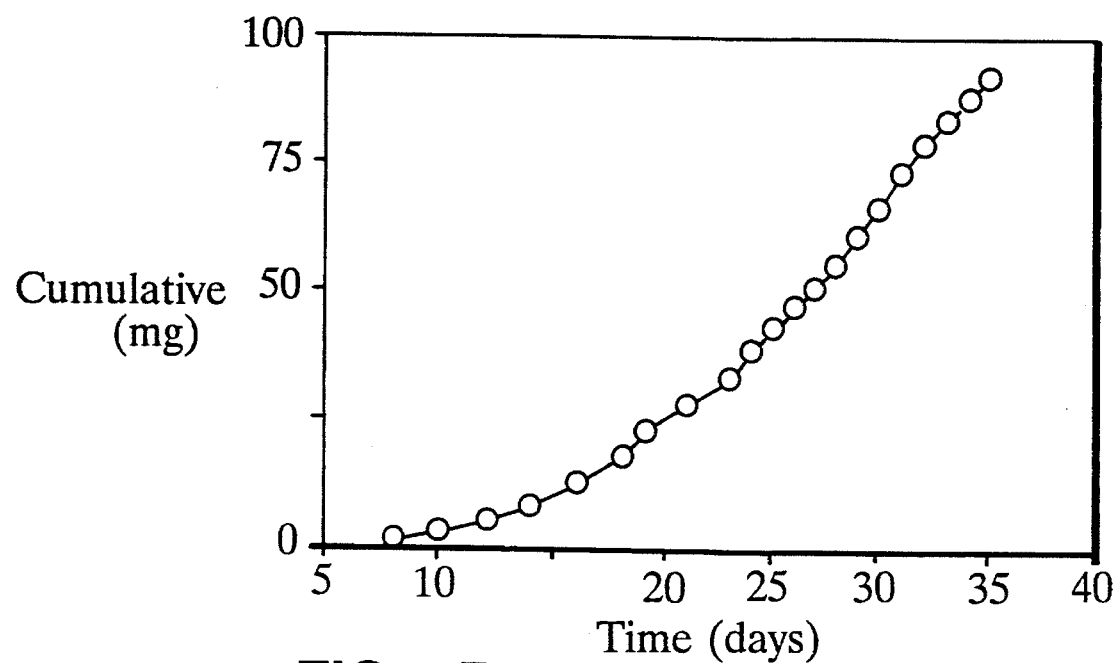

Expression of rMZ in BHK—Following methotrexate selection, ten resistant colonies were analyzed by Western blotting for their level of secretion of rMZ. Up to ten-fold variation was observed between individual clones. The highest secreting clone was cultured in a roller bottle containing 250 mL medium and without MTX selection. Aliquots were withdrawn each time the conditioned medium was collected and antigen levels were determined by ELISA using the conditioned medium from pNUT-transfected cells (no insert) as control and plasma-derived prothrombin as a standard. Levels of secretion of approximately 20 µg/mL were detected (FIG. 3a) and over a period of 35 days, approximately 90 mg of the protein were accumulated (FIG. 3b).

Recombinant protein purification—The recombinant meizothrombin (rMZ) was absorbed from the medium by addition of 1/25 volume of 0.4M sodium citrate, followed by 1/10 volume of 1.0 M $BaCl_2$ added slowly. The resulting suspension was stirred for 45 minutes at 22° C. The precipitate was collected by centrifugation (approximately 5,000×g, 4° C., 10 minutes) and the barium-citrate pellet was washed four times with successive volumes of 0.1M $BaCl_2$ comprising ½, ¼, ⅙ and ⅛ of the original medium volume. The absorbed protein was eluted by dissolving the pellet in 0.2 M EDTA (⅙ of the original medium volume). The solution was clarified by centrifugation and was subsequently dialyzed and concentrated against 20.0 mM Tris-HCl pH 7.4 using an Amicon ultrafiltration stirred cell with a PM10 membrane at 4° C. The protein was then subjected to anion exchange chromatography on a Pharmacia FPLC Mono-Q HR 5/5 column. The column was rinsed with 5.0 mL of starting buffer and the protein was eluted with a 0 to 1.0 M NaCl linear gradient in 20.0 mM Tris-HCl pH 7.4 at room temperature (26.0 mL total volume, flow rate 1.0 mL/min). rMZ eluted at approximately 0.45 M NaCl. The peak fractions, identified by absorbance at 280 nm, were pooled and dialyzed against 20.0 mM Tris-HCl, 0.15M NaCl pH 7.4 or diluted ¹⁄₁₀ with starting buffer. The sample was loaded onto the same FPLC column and eluted with a 0 to 30.0 mM CaCl₂ linear gradient in the same buffer at 4° C (15.0 mL total volume, flow rate 0.5mL/min). This step was performed to resolve fully γ-carboxylated from partially γ-carboxylated species of rMZ based on their $Ca^{++}$ binding properties (Yan, S. C. B., et al., Bio/Technology, 8:655–661, 1990). The first and main peak eluted at 15.0 mM CaCl₂ while the second peak extended between 18.0 and 25.0 mM CaCl₂. Fractions from each peak were pooled and protein concentrations were determined by absorbance readings at 280 nm ($E^{1\%}280$=13.8) (Mann, K. G., et al., Methods in Enzymol., 80:286–302, 1981).

Isolation and characterization of rMZ—Recombinant MZ isolated after barium citrate adsorption and ion-exchange FPLC was homogenous as judged by SDS-PAGE. These results suggest that a sub-population of the protein has less affinity for $Ca^{++}$, which may be the result of incomplete γ-carboxylation of the molecule. As was the case for plasma derived prothrombin, all material eluted on the $Ca^{++}$ gradient. The first and second peak fractions were pooled and are hereafter referred to as RMZ(I) and rMZ(II).

The amino-terminal sequence of rMZ was determined on an Applied Biosystems 473 pulse liquid protein sequencer, according to the manufacturer's protocol. Amino-terminal sequence analysis of the first five amino acids was performed on rMZ and indicated a sequence identical to that of human plasma prothrombin reflecting proper processing of the pre- and propeptides.

EXAMPLE 3

Analysis of the $Ca^{++}$ and Phospholipid Binding Properties of rMZ by Single Point Measurements of Fluorescence and Right Angle Light Scattering The $Ca^{++}$ binding properties of populations of rMZ were inferred by the decrement in intrinsic tryptophan fluorescence as described by Nelsestuen (Nelsestuen, G., J. Biol. Chem., 251:5648–5656, 1976) and Prendergast and Mann (Prenderegast, F. G., et al., J. Biol. Chem., 252:840–850, 1977). The sample of protein (1.6 mL, 30.0 µg/ml) in 0.02M HEPES, 0.15 M NaCl pH 7.4, was placed in quartz cuvette equipped with a microstirrer in a temperature regulated (22° C.) sample holder of a Perkin Elmer model MPF-66 fluorescence spectrophotometer. Intrinsic fluorescence was continuously monitored with $\lambda_{ex}$=280nm, $\lambda_{exm}$=340 nm, with respective excitation and emission band passes of 4 nm and 20 nm, and with a 290 nm cut-off filter in the emission beam. An aliquot (8.0 µL) of CaCl₂ was added to give a final concentration of 5.0 mM and the time course (approximately 5 minutes) of the fluorescence decrease was monitored. The progress curves were typified by an initial rapid exponential decrease followed by a modest linear decrease thereafter. The magnitude of the initial decrement was determined by extrapolation of the linear portion to the time of addition of CaCl₂.

The phospholipid binding properties of the populations of rMZ were inferred by right angle light scattering as described (Nelsestuen, G. L., et al., Biochemistry, 16:4164–4171, 1977; Bloom, J. W., et al., Biochemistry, 18:4419–4425, 1979). Aliquots of the proteins were dialyzed at 4 ° C. overnight against 0.1M HEPES, 0.075M NaCl, 5.0 mM EDTA, pH 7.4. The samples were then centrifuged at 12,000×g and 22° C. for 10 minutes to remove any particulate material. Samples of protein were then diluted into the same buffer (filtered, 0.2 µm) to a final concentration of 15.0 µg/mL in a thermally regulated (22° C.) quartz cuvette equipped with a microstirrer in the sample holder of the fluorescence spectrophotometer. The right angle scattering intensity at 320 nm was monitored continuously over time by setting the excitation and emission monochromators to 320 nm, both with 10 nm slit widths. An aliquot of concentrated PCPS vesicles was then added to yield a final PCPS concentration of 33.0 µg phospholipid/ mL. The addition of vesicles produced an immediate and stable increment in scattering. An aliquot (16.0 µL) of 1.0M CaCl₂ then was added to induce the $Ca^{++}$ dependent protein-phospholipid interaction. The time course of the change in scattering was monitored until a stable increment was obtained (<5 minutes). The fluorescence intensities before and after $Ca^{++}$ addition were averaged for two minutes each, with data collected at 0.1 second intervals.

Figure 4A:
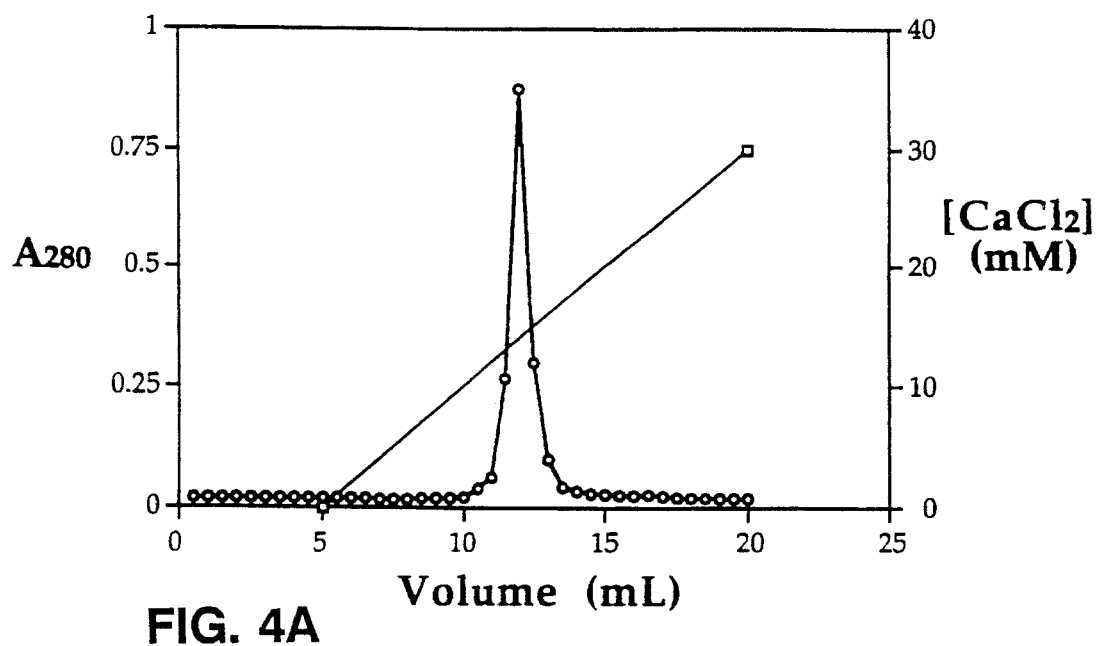
FIGS. 4(A and B) show the elution profile of plasma-derived prothrombin (pII) (A) and rMZ (B) during FPLC on a column of Mono Q (anion exchange).
Figure 4B:
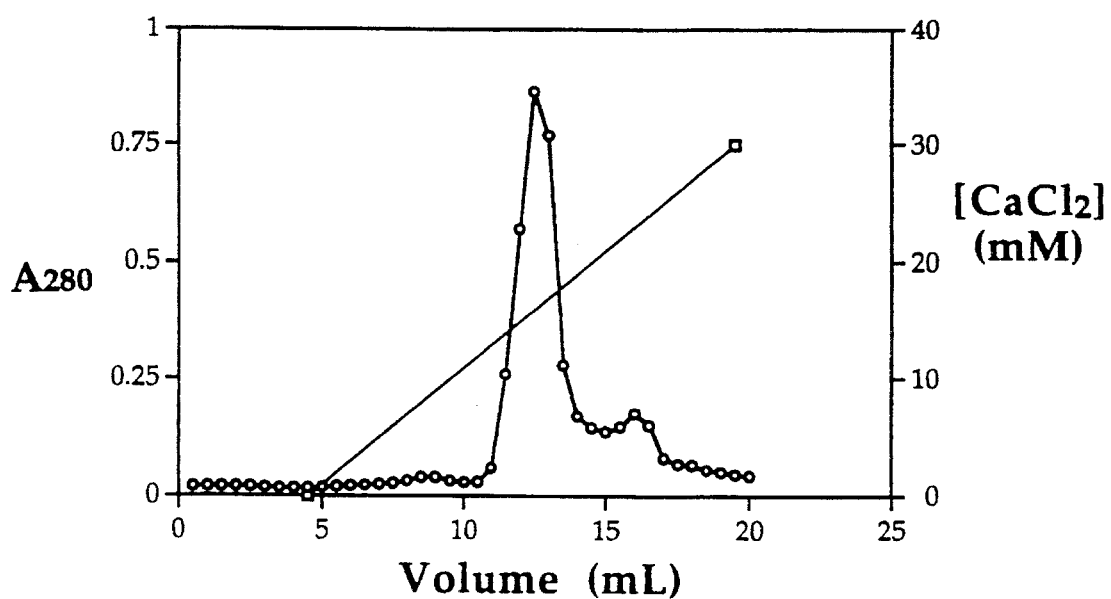
Figure 5A:
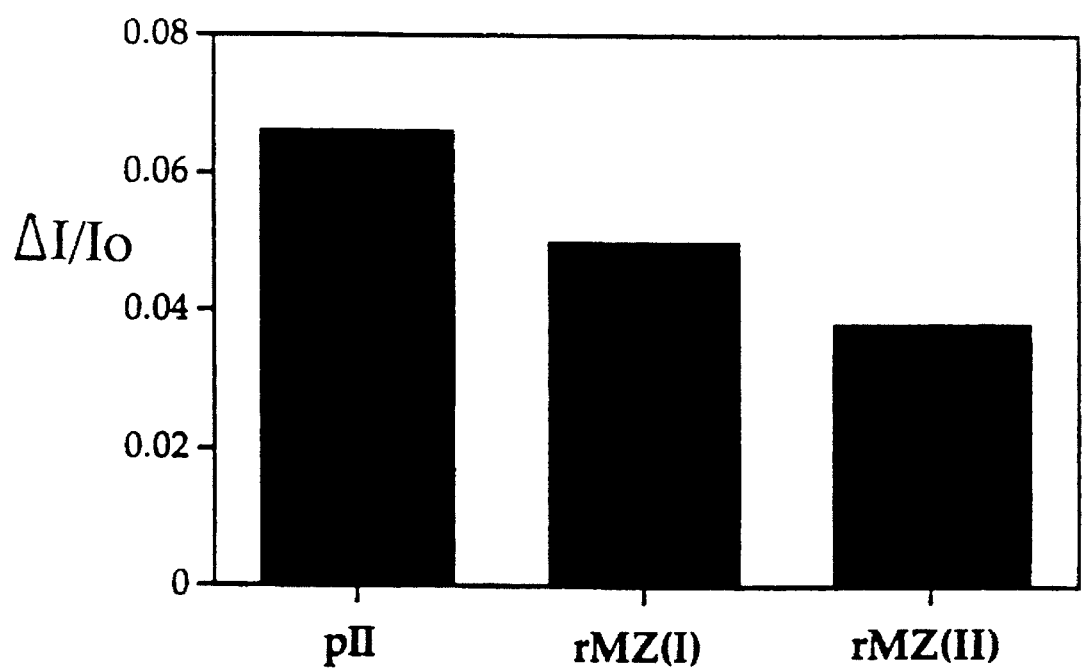
FIGS. 5a and 5b shows the fluorescence decrement in response to $Ca^{++}0$ (a) and light scattering intensity in response to PCPS vesicles binding (b).
Figure 5B:
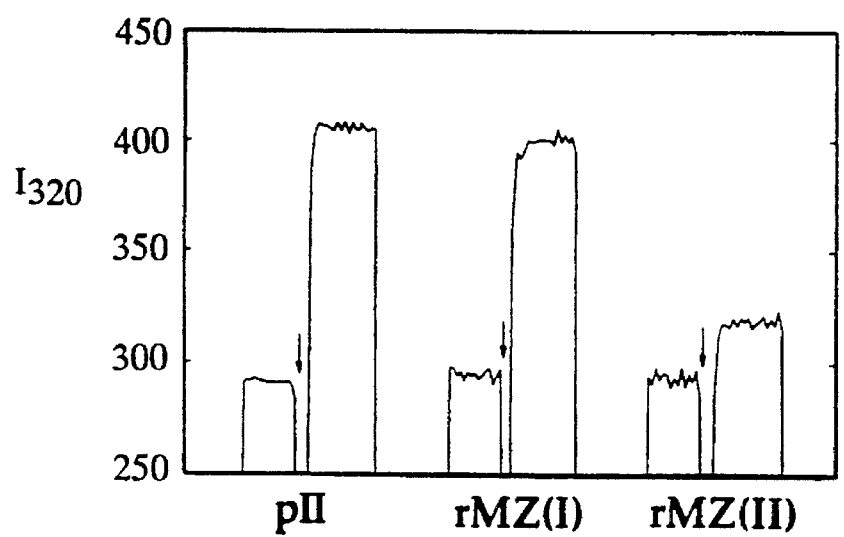

The increments in fluorescence and light scattering were compared to those obtained with plasma prothrombin under identical conditions in paired experiments.

rMZ(I) and rMZ(II) yielded increments of intrinsic fluorescence that were 76% and 58% of the value obtained with plasma derived prothrombin (FIG. 5a). Whether these differences imply the existence of sub populations which do not undergo a $Ca^{++}$ dependent conformational change, or an intrinsic difference in the molecules of the entire population cannot be ascertained from the present data. Clearly, however, the materials from both peaks rMZ(I) and rMZ(II) of the $Ca^{++}$ gradient can undergo similar, but not identical, $Ca^{++}$ dependent changes of conformation. In contrast, the phospholipid binding properties of the two fractions differed substantially. The increments in scattering intensity upon the addition of $Ca^{++}$ with rMZ(I) and rMZ(II) were 88% and 27%, respectively, of that observed with plasma-derived prothrombin (FIG. 5b). These data suggest that both populations eluted late in the second peak of the gradient did not retain the phospholipid binding properties of plasma derived prothrombin. These data also suggest that the chromatography method appears to distinguish and dissociate the $Ca^{++}$ binding from the phospholipid binding properties of rMZ and probably prothrombin. The decrement of intrinsic fluorescence in response to 5.0 mM $Ca^{++}$ of pII, and the materials of the two peaks obtained with rMZ upon chromatography in the $Ca^{++}$ gradient (rMZ (I) and rMZ (II), FIG. 4b) are indicated in (a). The increments in light scattering upon additions of $Ca^{++}$ to the solutions of the proteins and PCPS vesicles are shown in (b). These data indicate that rMZ (I) and rMZ (II) undergo a $Ca^{++}$-dependent change in conformation, albeit not identically. They also indicate that rMZ (I) binds PCPS nearly as well as pII, but rMZ (II) binds only weakly.

EXAMPLE 4

Activation of Human Prothrombin and rMZ(I) by the Prothrombinase Complex or Ecarin in the Presece and Absence of DAPA Reaction mixtures (2.4 mL) containing the protein sample (1.4 µM), 5.0 mM CaCl₂ and 10.0 µM PCPS with or without 3.0 µM DAPA were prepared in 20.0 mM Tris-HCl, 0.15 M NaCl pH 7.4, at 22° C. and were placed in a quartz cuvette equipped with a microstirrer in the sample holder of the fluorescence spectrophotometer. The reactions were initiated by the addition of either factor Xa (0.62 nM) or ecarin (1.3 µg/mL) and were monitored continuously by recording fluorescence intensity. When factor Xa was used, factor Va (2.0 nM) was included also. The presence of DAPA, measurements of extrinsic fluorescence of the DAPA-product complex were made with excitation and emission wavelengths of 335 and 545 nm, respectively, with respective slit widths of 10 and 20 nm, and a 430 nm cut-off filter in the emission beam. In the absence of DAPA, intrinsic fluorescence was monitored with excitation and emission wavelengths of 280 and 430 nm, respectively, with respective slit widths of 3 and 10 nm, and a 290 nm cut-off filter in the emission beam. The reactions were followed until a stable reading was reached, typically 10 to 25 minutes.

Activation of plasma prothrombin (pII) and rMZ(I) by the human prothrombinase complex in the presence of DAPA— The time courses of product formation upon activation of pII (trace a) and rMZ(I) (trace b), as indicated by fluorescence, are shown in FIG. 6a. Samples were withdrawn at times indicated by the inverted triangles in FIG. 6a and subjected to SDS-PAGE. Results with pII are shown in FIGS. 6c and 6e. The reaction (containing 1.4 μM pII or rMZ(I), 3.0 μM DAPA, 10.0 μM PCPS, 2.0 nM factor Va in 20 mM Tris-HCl, 0.15 M NaCl, pH 7.4 was initiated by the addition of factor Xa (0.62 nM final concentration). Fluorescence intensity was monitored at 545 nm with an excitation wavelength of 335 nm and data were recorded every 0.3 seconds (a). Samples of rMZ(I) and pII were withdrawn from ongoing activation and subjected to SDS-PAGE analysis before (b and c) and after (d and e) reduction of disulfide bonds with 2-mercaptoethanol. Sampling times with pII from left to right were 0.0, 0.65, 1.12, 1.62, 2.50, 4.35, 6.57, and 9.23 min (c and e), and with rMZ (I) were 0.0, 0.73, 1.57, 2.38, 3.37, 4.82, 7.28, and 14.42 min (b and d) after the addition of factor Xa. The abbreviations used for c and e are: pII, plasma-derived prothrombin; 1.2.A, Fragment 1.2.A chain; 1.2, Fragment 1.2; mIIa, plasma meizothrombin; mIIa 1, meizothrombin des F1; IIa, thrombin; IIa-B, thrombin B chain.

The gels indicated the presence of fragment 1.2 and thrombin which co-migrated under non-reducing conditions (FIG. 6c). Fragment 1.2, fragment 1.2A chain and the thrombin B chain were observed under reducing conditions (FIG. 6e). Minor quantities of prethrombin-1 or meizothrombin-des F1 also are evident in FIG. 6c. These patterns indicate the conversion of prothrombin to thrombin via meizothrombin and provide no evidence for accumulation of prethrombin-2 as an intermediate. The results with rMZ(I) are shown in FIGS. 6b and 6d. Under non-reducing conditions (FIG. 6b), a single band that co-migrates with prothrombin was observed at all sample times. Upon reduction, however, the prothrombin band progressively decreased in intensity and was replaced by bands migrating to the positions of the fragment 1.2 A chain and thrombin B chain. At the time of the last sample, consumption of rMZ(I) was substantial but not complete. The patterns indicate that a single prothrombinase catalyzed cleavage of rMz(I) at $Arg^{320}$—$Ile^{321}$ yielded the activated species rMZ(I)a, and that no further proteolysis catalyzed by rMZ(I)a occurred in the presence of DAPA.

Activation of pII was characterized by the appearance of a maximum at approximately 300 seconds and subsequent progression to a lower stable plateau. This profile indicates the transient formation of meizothrombin as an intermediate in the reaction, since meizothrombin-DAPA fluoresces 1.5 fold more intensely than thrombin-DAPA. In contrast, the profile with rMZ(I) increased monotonically and approached, at approximately 600 seconds, a plateau that was 1.54 fold greater than the plateau obtained with pII. In addition, the profiles were coincident for the first 160 seconds of the reaction, suggesting that initial rates of meizothrombin formation were similar with both substrates and that meizothrombin is the sole intermediate of prothrombin activation, as concluded by Krishnaswamy, et al.,(J. Biol. Chem., 261:8977– 8984, 198S).

Activation of plasma prothrombin (pII) and rMZ(I) by the human prothrombinase complex in the absence of DAPA— Because of DAPA, the data of FIG. 6 do not allow evaluation of the intrinsic stability or lack thereof of the intermediates to thrombin and meizothrombin catalyzed feedback cleavages. Thus, the experiments of FIG. 7 were performed in the absence of DAPA and activation was monitored by intrinsic fluorescence. The reaction containing 1.4 μM pII or rMZ(I), 10.0 μM PCPS, 2.0 nM factor Va in 20 mM Tris-HCl, 0.15 M NaCl, pH 7.4 was initiated by the addition of factor Xa (0.62 nM final concentration). Intrinsic fluorescence intensity was monitored at 340 nm ($\lambda_{ex}$=280 nm) and data were recorded every 0.3 seconds(a). Samples of rMZ(I) and pII were withdrawn from ongoing activations and subjected to SDS-PAE analysis before (b and c) and after (d and e) reduction of disulfide bonds with 2-mercaptoethanol. Sampling times from left to right were 0.0, 0.92, 1.73, 2.58, 3.95, 5.25, 7.13 and 9.57 min (c and e) and 0.0, 0.95, 1.80, 2.73, 4.67, 7.15, 9.33 and 16.1 min (b and d) after addition of factor Xa. The abbreviations used for c and e are as in the legend to FIG. 6. Included also are PI for prethrombin-1 and F1 for Fragment 1.

FIG. 7a indicates that activation of both pII (trace a) and rMZ(I) (trace b) by the prothrombinase complex are characterized by enhanced intrinsic fluorescence. Although the relative increment with pII is greater than that of rMZ(I), the absolute values at the end of the reactions were similar. The lower relative change with rMZ(I) reflects an initial value that exceeded the value with pII by a factor of 1.07 at identical substrate concentrations. Samples were withdrawn at times indicated by the inverted triangles and were subjected to SDS-PAGE under non-reducing and reducing conditions. Gels with plasma prothrombin indicated consumption of prothrombin, formation of thrombin and extensive thrombin feedback, as evidenced by the accumulation of meizothrombin(desF 1) and fragment 1 (FIG. 7c, 7e). In contrast, results with rMZ(I) indicated a single band in all samples under non-reducing conditions (FIG. 7b) and the sole formation of fragment 1.2 A chain and thrombin B chain under reducing conditions (FIG. 7d). These latter data indicate that rMZ(I), unlike pII, is stable with respect to feedback proteolysis. The gels were analyzed by laser densitometry and the results showed that the initial rate of consumption of plasma prothrombin was 1.5 fold greater than that of rMZ(I).

Figure 8A:
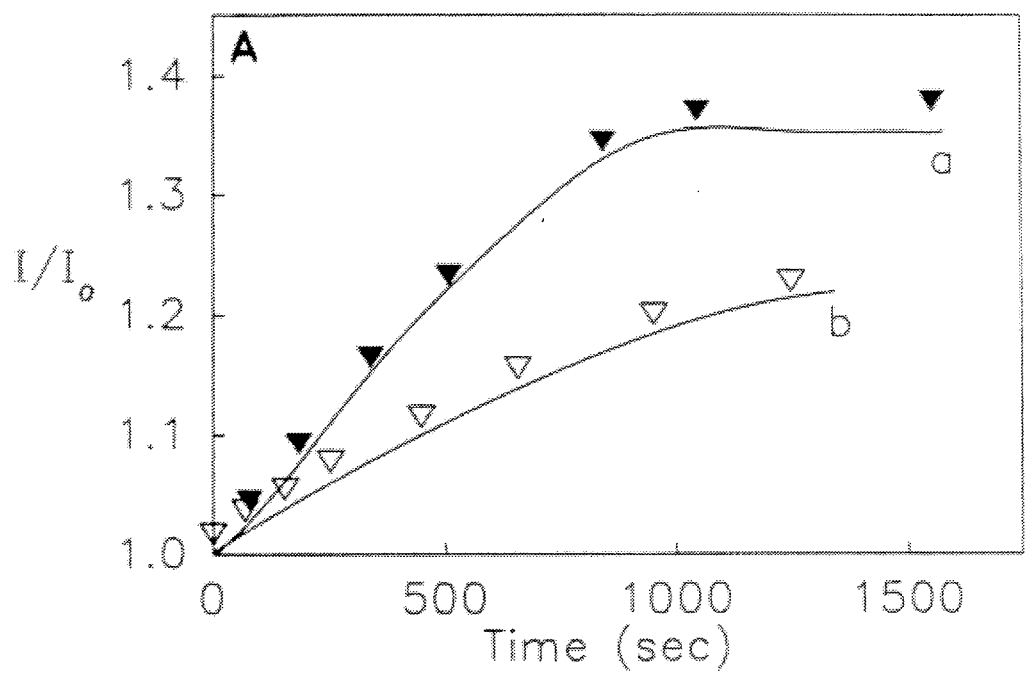
FIGS. 8A–8E show ecarin-catalyzed activation of prothrombin (pII) and rMZ(I) monitored by intrinsic fluorescence (A) and SDS-PAGE (B–E).

Activation of plasma prothrombin and rMZ(I) by ecarin— The activation of pII or rMZ(I) by the prothrombin activator of E. carinatus venom, ecarin, was monitored by intrinsic fluorescence in the absence of DAPA. The time courses of intrinsic fluorescence are exhibited in FIG. 8a trace a, pII; trace b, rMZ(I). The reaction containing 1.4 μM pII or rMZ(I), 10.0 μM PCPS, in 20 mM Tris-HCl, 0.15 M NaCl pH 7.4 was initiated by the addition of ecarin (1.3 μg/mL final concentration). Intrinsic fluorescence intensity was monitored at 340 nm ($\lambda_{ex}$=280 nm) and data were recorded every 0.3 seconds (a). Samples of rMZ(I) and pII were withdrawn from ongoing activations and subjected to SDS-PAGE analysis before (b and c) and after (d and e) reduction of disulfide bonds with 2-mercaptoethanol. Sampling times from left to right were 0.0, 2.0, 5.58, 8.38, 13.0, 16.4, 19.0 and 23.7 min (c and e) and 0.0, 1.22, 2.62, 4.23, 7.50, 9.33, 14.92 and 24.58 min (b and d) after addition of ecarin. The abbreviations used for c and e are as described for FIG. 7 above.

Analysis of prothrombin/rMZ(I) activation by gel electrophoresis in SDS—From the above reactions, aliquots of 100.0 μL were withdrawn at intervals and added to 200.0 μL of 0.2 M acetic acid. These solutions were then lyophilized and the residues dissolved in 50.0 μL of 5.0 mM EDTA, 0.5% (w/v) Bromophenol Blue, 10% (v/v) glycerol and 1% (w/v) SDS. The reconstituted samples were divided in two equal aliquots and 2-mercaptoethanol (1.0 μL) was added to one of the aliquots. Both were heated at 90° C. for 2 minutes and subjected to electrophoresis in 5–15% polyacrylamide gradient gels using the buffers and conditions described by Neville (Neville, D. M., J. Biol. Chem., 246:6328– 6334, 1971). The gels were stained with Coomassie Brilliant Blue and destained by diffusion. In some instances gels were scanned with an LKB model 2202 laser densitometer.

Figures 8B, 8C:
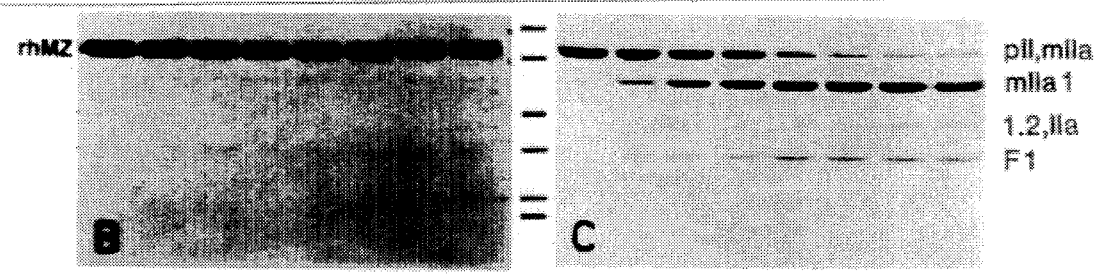
Figures 8D, 8E:
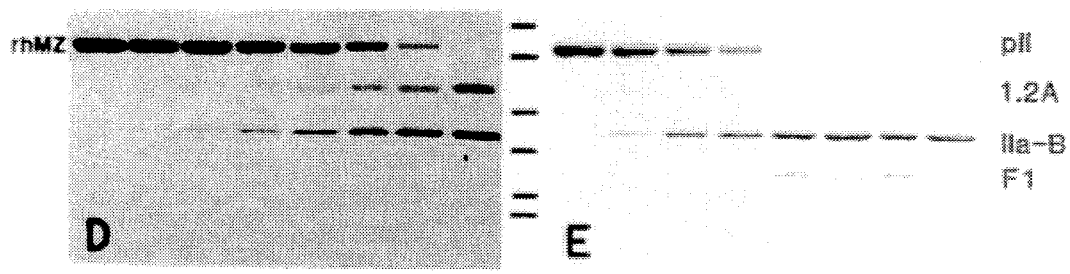

In both instances the reactions were marked by an increase in signal, similar to those observed with prothrombinase (FIG. 7a). Samples were removed at various times (inverted triangles) and subjected to SDS-PAGE under reducing and non-reducing conditions. With pII, the predominant species were meizothrombin(desF1) (FIG. 8c) and thrombin B chain plus fragment 1 (FIG. 8e), indicating substantial feedback proteolysis. With rMZ(I), the products were indistinguishable from those obtained with prothrombinase, and were similarly stable. Laser densitometry of the gels showed that the initial rate of consumption of plasma prothrombin exceeded that of rMZ(I) by a factor of 1.24.

EXAMPLE 5

Preparation of rhMAa after Activation by Ecarin

The snake venom activator, ecarin, must be removed from activated rhMZa prior to experimental use in subjects. rhMZ(I) isolated from the $Ca^{++}$ gradient was dialyzed against 75% ammonium sulfate and the precipitate resuspended in 50% glycerol. For the isolation of active rMZ(I), the protein (~2 mg) was resuspended in 10 mL of 20 mM Tris-HCl, 0.15M NaCl, 5 mM $CaCl^2$ pH 7.4. Approximately 17 μg of ecarin was added and the suspension was shaken gently for 25 minutes at 22° C. The activation was followed either by fluorescence or by assaying amidolytic activity with S-2238 as described previously. rhMZ(I)a was recovered by chromatography on benzamidine-sepharose. The column was equilibrated and washed with 15 mL of 20 mM Tris-HCl, 0.15M NaCl, pH 7.4, and eluted with 7.5 mM benzamidine in the same buffer (flow rate ~2 mL/min). Fractions of 1 mL were collected and the protein was detected using Biorad Bradford microassay procedure. The fractions containing the active protein were pooled and dialyzed against 20 mM Tris-HCl, 0.15M NaCl, pH 7.4 prior to precipitation against 75% ammonium sulfate. The precipitate was then resuspended in 50% glycerol and kept at −20° C. until used.

EXAMPLE 6

Functional Properties of rMZ(I)

rhMZ(I) was activated by either prothrombinase or ecarin and assayed for esterase, amidolytic and fibrinogen clotting activities. Results were compared to samples of plasma prothrombin that were activated under identical conditions.

Fibrinogen clotting assays—In a 10×75 mm glass tube the following were added: 100.0 μL of human fibrinogen (2.0 mg/mL) dissolved in 0.02M Tris-HCl, 0.15M NaCl, pH 7.4 and 100.0 μL of 20.0 mM Tris-HCl, 0.15M NaCl, 5.0 mM $CaCl_2$, pH 7.4. The contents were equilibrated at 37° C., (approximately 30 seconds) and the reaction was initiated by the addition of 20.0 μL of sample (fully activated plasma prothrombin or rMZ(I)a) at various dilutions in assay buffer containing 0.01% tween-80. The time required for clot formation was determined manually at 37° C.

Esterase assays—A cuvette containing 0.87 mL of 50 mM Tris-HCl, pH 8.1 and 30.0 μL of sample (fully activated plasma prothrombin or rMZ(I)a) at a final concentration of 0.14 μM was maintained at 22° C. in a quartz cuvette in the sample compartment of a Perkin-Elmer λ4B spectrophotometer. The reaction was initiated by addition of 0.1 mL of 0.01M TAME (in $H_2O$) and followed at 247 nm at 30 second intervals for 10 minutes. An extinction coefficient of 409 $M^{-1}$ $cm^{-1}$ for the TAME hydrolysis product was used for calculations.

Amidolytic assays—Samples (fully activated plasma prothrombin or rMZ(I)a) were diluted in 20.0 mM Hepes, 0.15M NaCl, 0.01% tween-80 pH 7.4 and 50.0 μL aliquots were pipetted into the wells of a microtitre plate. The solutions were warmed to 37° C. and the assays were initiated by the addition of 50 μL of 0.4 mM S-2238 dissolved in assay buffer. The conversion of S-2238 was followed by monitoring the absorbance at 405 nm at 30 second intervals for 10 minutes at 37° C., using a Titre-Tek Twin reader (Flow Laboratories).

The results are presented in Table 2. Recombinant hFII demonstrated 57.4% of the clotting activity of plasma prothrombin (pII). A lower activity was expected for rhFII due to the partial conversion to prethrombin-1 and the incomplete state of γ-carboxylation of the protein, which might lead to incomplete activation. rMZ(I) activated by either prothrombinase or ecarin demonstrated 6.8% of the clotting activity of plasma prothrombin. Plasma prothrombin activated with ecarin (to yield predominantly meizothrombin), and rMZ(I) activated with either prothrombinase or ecarin, exhibited identical TAME esterase activities. These were two-fold greater than that obtained with plasma prothrombin activated with prothrombinase. rMZ(I) activated with either prothrombinase or ecarin yielded similar amidolytic activities, which were approximately one half the activity obtained with plasma prothrombin treated with either activator. rhQM appeared to inhibit the reaction, leading to a clotting time longer then the one observed in the absence of protein (See buffer control). Although their level of γ-carboxylation was probably not complete the mutant proteins can interact with the prothrombinase complex, thereby occupying sites, which decreases the rate of the reaction.

TABLE 2

ESTERASE, AMIDOLYTIC AND FIBRINOGEN CLOTTING ACTIVITY

|  | TAME | S-2238 | Relative Clotting Activity |
|---|---|---|---|
| pII + PASE | 16 ± 2 | 129 ± 3 | 1.000 |
| rMZ(I) + PASE | 3 ± 4 | 60 ± 1 | 0.068 |
| pII + ECARIN | 30 ± 4 | 119 ± 12 | 0.000 |
| rMZ(I) + ECARIN | 31 ± 2 | 76 ± 5 | 0.068 |
| rhQM | 0.000 | 0.000 | <0* |
| Control | 0.000 | 0.000 | 0.000 |

*Clotting time longer than buffer control
Abbreviations: pII, human plasma-derived prothrombin; rMZ (I), recombinant mutant human prothrombin (R155A, R271A, R284A) peak I; PASE, human prothrombinase complex.

EXAMPLE 7

Stability of rhMZ activated by Prothrombinase

Figure 9A:
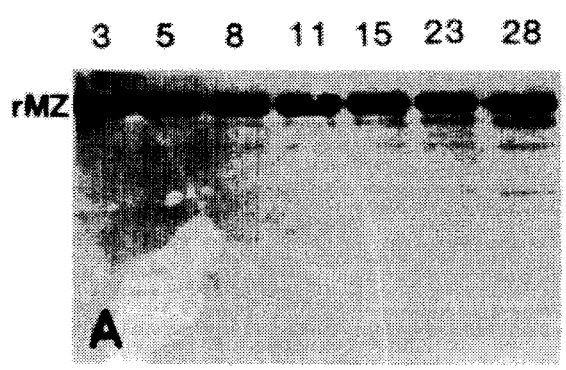
FIGS. 9(A and B) show the stability of rMZ(I)a as analyzed by SDS-PAGE (A-nonreducing; B-reducing gel).
Figure 9B:
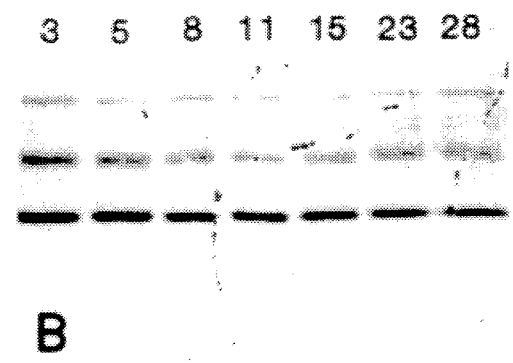

A sample of rMZ(I) was activated with prothrombinase and the reaction mixture was subsequently stored at 4° C. After 3, 5, 8, 11, 15, 23 and 28 days, aliquots (100 μL) were withdrawn and prepared for SDS-PAGE. On day 28, electrophoresis was performed and the remaining solution was assayed for amidolytic (S- 2238) and esterase (TAME) activities. Results of electrophoresis under nonreducing and reducing conditions are shown respectively in FIGS. 9a and 9b. A sample of rMZ(I) activated with prothrombinase as described for FIG. 7 was stored at 40C. Samples withdrawn 3, 5, 8, 11, 15, 23, and 28 days later were analyzed by SDS-PAGE without (a) and with (b) reduction of disulfide bonds.

The gels show that rMZ(I)a is highly resistant to thrombin-like feedback proteolysis over the 28 day period, although after about 8 days of storage low amounts of unidentified degradation products were visible and these accumulated over time.

The functional assays showed that the esterase and amidolytic activities after 28 days were respectively 81% and 53% of the activities measured immediately following activation.

EXAMPLE 8

Studies with rhQM

Recombinant QM was purified as described for rMZ (See Example 2) and the fully λ-carboxylated species rQM(I) was isolated on the CaCl$_2$ gradient. Human plasma prothrombin fragment 1 was isolated as described previously (Stevens and Nesheim, Biochem, 32:2787, 1993. To a microcuvette were added factor Va (2 nM), PCPS vesicles (10 μM), CaCl$_2$ (5 mM), DAPA (1.5 μM), human thrombin (0.5 μM) (final concentrations in TBS pH 7.4, final volume: 200 μL) and various equimolar ratios of rQM(I) or human prothrombin fragment 1 (F 1) in 50% glycerol. Because the stock solution of rQM(I) and F1 were in 50% glycerol, the negative control and the assays were all performed in the presence of an equal volume of 50% glycerol. The reactions were initiated by the addition of factor Xa (1 nM) and were monitored continuously by recording fluorescence intensity. The excitation and emission wavelengths were 280 and 545 nm respectively.

Figure 10:
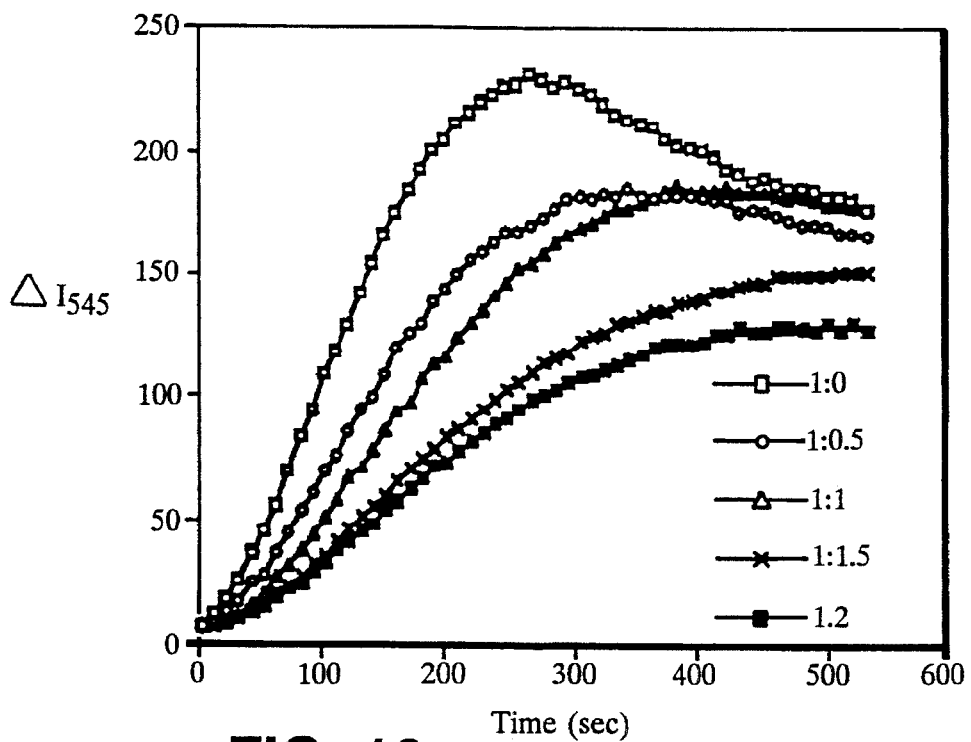
FIG. 10 shows the inhibition of prothrombin activation by various amounts of rhQM.

Inhibition by rhQM—rhQM inhibited clotting in a prothrombin deficient clotting assay. To further investigate this observation, the activation of prothrombin by the prothrombinase complex was monitored by DAPA fluorescence, in the presence of rhQM (FIG. 10) (See Example 3). The profile of prothrombin activation in the absence of rhQM (ratio 1:0) demonstrated the characteristic increment in fluorescence (at approximately 300 sec) followed by a progression toward a stable plateau. Upon addition of various amounts of rhQM to the reaction, a decrease in the rate of activation was observed, but a maximum fluorescence was still reached at approximately 370 seconds. As more rhQM was added to the reaction, the rate of conversion was further decreased and the profile changed. The increase in fluorescence became monotonic and approached a plateau that was lower then that obtained with prothrombin alone. The initial rate of reaction appeared directly proportional to the concentration of rhQM in the reaction. Although rhQM clearly inhibited the activation of prothrombin by the prothrombinase complex, the mechanism of the inhibition is unclear.

Figure 11:
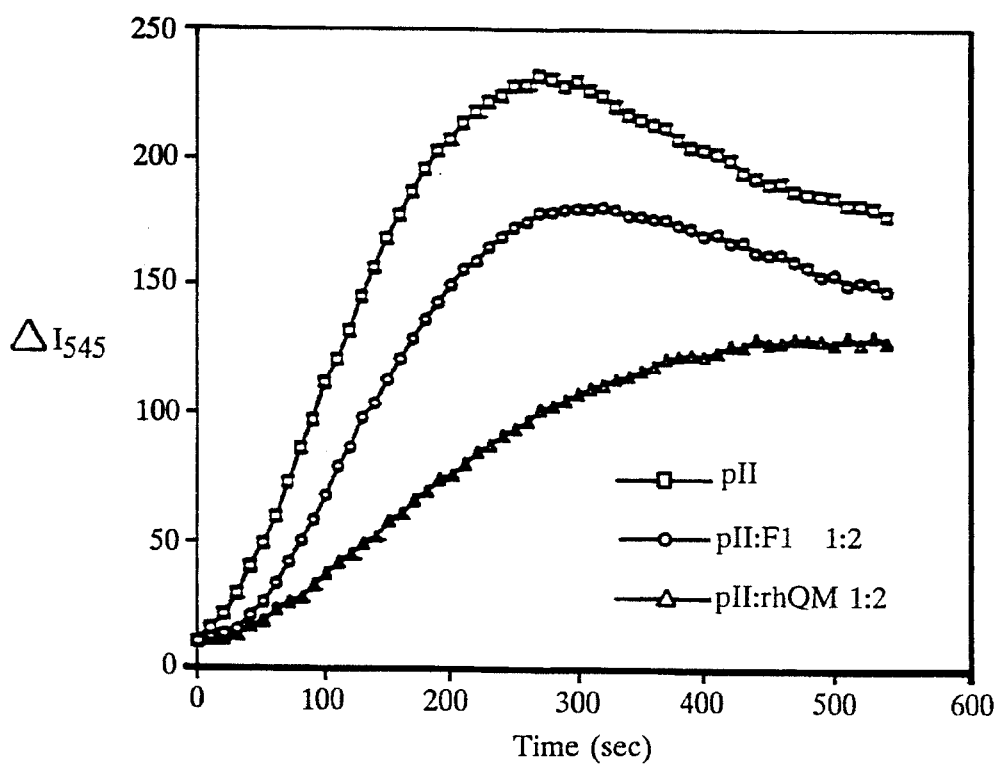
FIG. 11 shows the inhibition of pII activation by rhQM and F1 in the presence of DAPA.

The experiment was repeated in the presence of prothrombin fragment 1 (F1) (FIG. 11 ). F1 contains the Gla domain and the first kringle of prothrombin. If the inhibition by rhQM was simply due to competition between prothrombin and rhQM for interaction with the complex through the Gla domain, F1 should affect the reaction similarly. FIG. 11 illustrates the time course of prothrombin activation in the presence of equimolar amount of rhQM or F1, at a 2:1 ratio with prothrombin.

The quadruple mutant prothrombin, rhQM, showed the highest level of expression ever reported for a fibrinolysis or coagulation protein, in a mammalian expression system.

As was expected, the quadruple mutant was not cleaved by FXa, and did not demonstrate any proteolytic or clotting activity. Functional assays (Table 2) revealed that rhQM increased the clotting of prothrombin deficient plasma. Because rhQM is structurally similar to prothrombin, it probably interacted with the prothrombinase complex and slowed further reaction. Since rhQM will not be cleaved, it may not dissociate as readily as thrombin. The greater inhibition of prothrombin activation by rhQM than fragment 1 revealed that the presence of the Gla domain was not the only component of the interaction (FIG. 11). Bovine factor V heavy chain interactions with bovine prothrombin or prethrombin- 1 exhibit the same dissociation constant (Luchow, et al, Biochem, 28:2348, 1989). This indicates that the fragment 1 portion of prothrombin does not influence the association with FVa. The interaction between rhQM and FVa within the prothrombinase complex might therefore further inhibit activation of prothrombin to thrombin. The inhibition of prothrombin activation by rhQM could be interpreted as anticoagulant activity by means of preventing coagulation.

Recombinant meizothrombin proved to be extremely stable and resistant to further degradation. Neither ecarin nor factor Xa was capable of catalyzing the hydrolysis of the modified cleavage sites, even over long periods of time. rhMZa can therefore be stored for extended periods of time. This eliminates the ambiguities surrounding the possible presence of meizothrombin(desF1) or thrombin in the meizothrombin preparation, and potential effects of inhibitors such as DAPA in studies of the functional properties of meizothrombin generated from plasma prothrombin. The only ambiguity remains the effect of replacing three charged residues by alanine on the conformation of the molecule; because the activation sites are probably on the surface of the zymogen molecule (and accessible to proteases), these minor changes would be expected to have little or no effect on the overall conformation of the zymogen.

Although the invention has been described with reference to the presently preferred embodiment, it should be understood that various modifications can be made without departing from the spirit of the invention. Accordingly, the invention is limited only by the following claims.

Sequence ID Listing

Sequence ID Nos. 1–8 are nucleotide sequences for oligonucleotides used for PCR, found in Table 1, page 22.

We claim:

1. An isolated polynucleotide which encodes a polypeptide characterized by:

(a) having anti-coagulant activity; and (b) having the amino acid sequence of prothrombin with amino acid substitutions at residues 155, 271 and 284.

2. A host cell which contains the polynucleotide of claim 1.

3. A recombinant expression vector which contains the polynucleotide of claim 1.

4. The vector of claim 3, wherein the vector is a plasmid.

5. The vector of claim 3, wherein the vector is a virus.

6. A method for producing a polypeptide, having anticoagulant activity and having the amino acid sequence of prothrombin with amino acid substitutions at residues 155, 271, and 284 which, upon activation, stimulates production of activated protein C, comprising:

(a) introducing into a host cell an expression vector which contains a nucleotide sequence which encodes the polypeptide, which, upon activation, stimulates production of activated protein C;

(b) culturing the host cell in an appropriate medium; and (c) isolating the polypeptide product encoded by the expression vector.

7. The method of claim 6, further comprising cleaving the polypeptide with a protease.

8. The method of claim 7, wherein the protease is ecarin.

9. The method of claim 7, wherein the protease is prothrombinase complex or components thereof.

10. The method of claim 6, wherein the polypeptide is meizothrombin.

11. The method of claim 6, wherein the expression vector contains a phenotypic selection marker nucleotide sequence.

12. The method of claim 6, wherein the host cell is a eukaryote.

13. The method of claim 12, wherein the host cell is a mammalian cell.

14. The method of claim 13, wherein the mammalian cell is selected from the group consisting of COS, BHK, 293, HepG2, CV-1, and CHO cells.

15. A method for producing a polypeptide having an amino acid sequence of prothrombin with amino acid substitutions at residues 155, 271, 284, and 320 which acts as an inactive prothrombin molecule which is incapable of activation comprising:

(a) introducing into a host cell an expression vector which contains a nucleotide sequence which encodes a polypeptide having an amino acid sequence of prothrombin with amino acid substitutions at residues 155, 271, 284, and 320;

(b) culturing the host cell in an appropriate medium; and (c) isolating the polypeptide product encoded by the expression vector.

16. The method of claim 15, wherein the expression vector contains a phenotypic selection marker nucleotide sequence.

17. The method of claim 15, wherein the host cell is a prokaryote.

18. The method of claim 15, wherein the host cell is a eukaryote.

19. The method of claim 18, wherein the host cell is a mammalian cell.

20. The method of claim 19, wherein the mammalian cell is selected from the group consisting of COS, BHK, 293, HepG2, CV-1, and CHO cells.

* * * * *